US009347085B2

(12) United States Patent
Gan et al.

(10) Patent No.: US 9,347,085 B2
(45) Date of Patent: May 24, 2016

(54) METHODS AND COMPOSITIONS FOR REDUCING AMYLOID BETA LEVELS

(71) Applicant: The J. David Gladstone Institutes, San Francisco, CA (US)

(72) Inventors: Li Gan, Burlingame, CA (US); Lennart Mucke, San Francisco, CA (US)

(73) Assignee: The J. David Gladstone Institutes, San Francisco, CA (US)

(*) Notice: Subject to any disclaimer, the term of this patent is extended or adjusted under 35 U.S.C. 154(b) by 0 days.

(21) Appl. No.: 14/219,556

(22) Filed: Mar. 19, 2014

(65) Prior Publication Data

US 2014/0234302 A1    Aug. 21, 2014

Related U.S. Application Data

(62) Division of application No. 13/847,092, filed on Mar. 19, 2013, now Pat. No. 8,691,519, which is a division of application No. 12/447,241, filed as application No. PCT/US2007/024059 on Nov. 15, 2007, now Pat. No. 8,420,613.

(60) Provisional application No. 60/859,326, filed on Nov. 15, 2006.

(51) Int. Cl.
| | |
|---|---|
| *G01N 33/53* | (2006.01) |
| *A61K 39/00* | (2006.01) |
| *A61K 39/395* | (2006.01) |
| *C12Q 1/37* | (2006.01) |
| *A61K 38/55* | (2006.01) |
| *C07K 16/38* | (2006.01) |
| *C12N 15/113* | (2010.01) |
| *G01N 33/68* | (2006.01) |
| *A61K 31/7052* | (2006.01) |
| *C12Q 1/68* | (2006.01) |
| *A61K 38/00* | (2006.01) |

(52) U.S. Cl.
CPC ............ *C12Q 1/37* (2013.01); *A61K 31/7052* (2013.01); *A61K 38/00* (2013.01); *A61K 38/55* (2013.01); *A61K 39/3955* (2013.01); *C07K 16/38* (2013.01); *C12N 15/1136* (2013.01); *C12N 15/1137* (2013.01); *C12Q 1/68* (2013.01); *G01N 33/6896* (2013.01); *C12N 2310/14* (2013.01); *C12N 2310/531* (2013.01); *C12N 2330/51* (2013.01)

(58) Field of Classification Search
CPC ...... A61K 39/00; A61K 39/395; G01N 33/53
USPC .................. 435/7.1; 424/133.1, 7.1
See application file for complete search history.

(56) References Cited

U.S. PATENT DOCUMENTS

| | | | | |
|---|---|---|---|---|
| 8,263,416 | B2* | 9/2012 | Sunde et al. | .................. 436/518 |
| 8,420,613 | B2 | 4/2013 | Gan et al. | |
| 8,691,519 | B2 | 4/2014 | Gan et al. | |
| 2004/0086979 | A1* | 5/2004 | Zhang et al. | ............... 435/70.21 |
| 2004/0248232 | A1 | 12/2004 | Hook | |

FOREIGN PATENT DOCUMENTS

| | | |
|---|---|---|
| WO | WO 2004/084830 | 10/2004 |
| WO | WO 2005/037221 | 4/2005 |
| WO | WO 2005/059100 | 6/2005 |

OTHER PUBLICATIONS

Hasegawa et al. Regulation of Glial Development by Cystatin C; Journal of Neurochemistry, vol. 100 (Oct. 26, 2006) pp. 12-22.*
Fukuzaki et al. Ovariectomy Increases Neuronal Amyloid-Beta Binding Alcohol Dehydrogenase Level in the Mouse Hippocampus, Neurochemistry International, vol. 52 (2008) pp. 1358-1364.*
Teng et al. Construction and Testing of Mouse-Human Heteromyelomas for Human Monoclonal Antibody Production; vol. 80 (1983) pp. 7308-7312.*
Anonymous, "Cystatin C's Naughty Side-Slowing A(beta) Degradation by Cathepsin B", Alzforum (2008), pp. 1-3.
Bernstein et al., "The Possible Place of Cathepsins and Cystatins in the Puzzle of Alzheimer Disease: a Review", Mol. Chem. Neuropathol. (1996), 27(3):225-47.
Cataldo et al., "Enzymatically Active Lysosomal Proteases are Associated with Amyloid Deposits in Alzheimer Brain", Proc. Natl. Acad. Sci. USA (1990), 87:3861-3865.
Cataldo et al., "Increased Neuronal Endocytosis and Protease Delivery to Early Endosomes in Sporadic Alzheimer's Disease: Neuropathologic Evidence for a Mechanism of Increased Beta-Amyloidogenesis", J. Neurosci. (1997), 17:6142.
Dorfman et al., "Differential Cerebral Deposition of IDE and NEP in Sporadic and Familial Alzheimer's Disease", Neurobiology of Aging (2010), 31(10):1743-1757.
Farris et al., "Insulin-degrading Enzyme Regulates the Levels of Insulin, Amyloid Beta-protein, and the Beta-amyloid Precursor Protein Intracellular Domain in vivo", PNAS (2003), 100(4):4162-4167.
Hammond et al., "Post-Transcriptional Gene Silencing by Double-Stranded RNA", Nature Reviews Genetics (2001), 2(2):110-119.
Hook et al., "Beta-Secretases for Production of Beta-Amyloid in the Major Regulated Secretory Pathways are Identified as Cathepsins B and L: Implications for Cysteine Proteases as Drug Targets for AD", Alzheimer's & Dementia: The Journal of Alzheimer's Association (2005), 1(1):74-75.

(Continued)

*Primary Examiner* — Kagnew H Gebreyesus
*Assistant Examiner* — Paul Martin
(74) *Attorney, Agent, or Firm* — Michael B. Rubin; Bozicevic, Field & Francis LLP

(57) ABSTRACT

The present invention provides methods for reducing the level of amyloid beta protein in a cell or tissue, the methods generally involving contacting the cell or tissue with an agent that reduces cystatin C levels and/or activity. The present invention provides methods for treating Alzheimer's disease (AD), and methods for treating cerebral angiopathy, in an individual, the methods generally involving administering to an individual having AD a therapeutically effective amount of an agent that reduces cystatin C levels and/or activity. The present invention further provides methods for identifying an agent that reduces cystatin C levels and/or activity.

21 Claims, 17 Drawing Sheets

(56) References Cited

OTHER PUBLICATIONS

Hook et al., "Cystein Protease Inhibitors Effectively Reduce in Vivo Levels of Brain Beta-Amyloid Related to Alzheimer's Disease", Biol. Chem. (2007), 388(2):247-52.

Hook et al., "Inhibition of Cathepsin B Reduces Beta-Amyloid Production in Regulated Secretory Vesicles of Neuronal Chromaffin Cells: Evidence for Cathepsin B as a Candidate Beta-Secretase of Alzheimer's Disease", Biol. Chem. (2005), 386:931-940.

Hook, "Neuroproteases in Peptide Neurotransmission and Neurodegenerative Diseases: Applications to Drug Discovery Research", BioDrugs (2006), 20:105-119.

Hook, Unique Neuronal Functions of Cathepsin L and Cathepsin B in Secretory Vesicles: Biosynthesis of Peptides in Neurotransmission and Neurodegenerative Disease., Biol. Chem. (2006), 387:1429-1439.

Kaeser et al., "Cystatin C Modulates Cerebral Beta-amyloidosis", Nature Genetics (2007), 39(12):1437-1439.

Kaeser et al., "Cystatin C Modulates Cerebral B-Amyloidosis—Supplementary Figures", Nature Genetics (2007), pp. 1-13.

Kaeser et al., Supplementary Tables, Nature Genetics (2007), 38(12-13).

Levy et al., "The Role of Cystatin C in Cerebral Amyloid Angiopathy and Stroke: Cell Biology and Animal Models", Brain Pathol. (2006), 16(1):60-70.

Mackay et al., "A Possible Role for Cathepsins D, E, and B in the Processing of Beta-Amyloid Precursor Protein in Alzheimer's Disease", Eur. J. Biochem. (1997), 244:414-425.

Mi et al., "Cystatin C Inhibits Amyloid-Beta Deposition in Alzheimer's Disease Mouse Models", Nat. Genet. (2007), 39(12):1440-2.

Mueller-Steiner et al., "Antiamyloidogenic and Neuroprotective Functions of Cathepsin B: Implications for Alzheimer's Disease", Neuron (2006), 51:703-714.

Nagai et al., "Cystatin C and Cathepsin B in CSF from Patients with Inflammatory Neurologic Diseases", Neurology (2000), 55(12):1828-32.

Nagai et al., "Neuronal Cell death Induced by Cystatin C in Vivo and in Cultured Human CNS Neurons is Inhibited with Cathepsin B", Brain Research (2005), 1066:120-128.

Nakagomi et al., "Isolation of Novel Peptides, Cabin-1, -2, -3, and -4, that Inhibit Cathepsin B from a Thermolysin Digest of Human Plasma", Biol. Pharm. Bull. (2002), 25:564-568.

Nycander et al., "Two-Step Mechanism of Inhibition of Cathepsin B by Cystatin C due to Displacement of the Proteinase Occluding Loop", FEBS Lett (1998), 422(1):61-4.

Sun et al., "Cystatin C-Cathepsin B Axis Regulates Amyloid Beta Levels and Associated Neuronal Deficits in an Animal Model of Alzheimer's Disease", Neuron (2009), 60(2):247-257.

Wikipedia contributors, "Amyloidosis", Wikipedia, The Free Encyclopedia (Jul. 2011), Web.

Wilcock et al., "Deglycosylated Anti-Amyloid-Beta Antibodies Eliminate Cognitive Deficits and Reduce Parenchymal Amyloid with Minimal Vascular Consequences in Aged Amyloid Precursor Protein Transgenic Mice", Journal of Neuroscience (2006), 26:5340-5346.

* cited by examiner

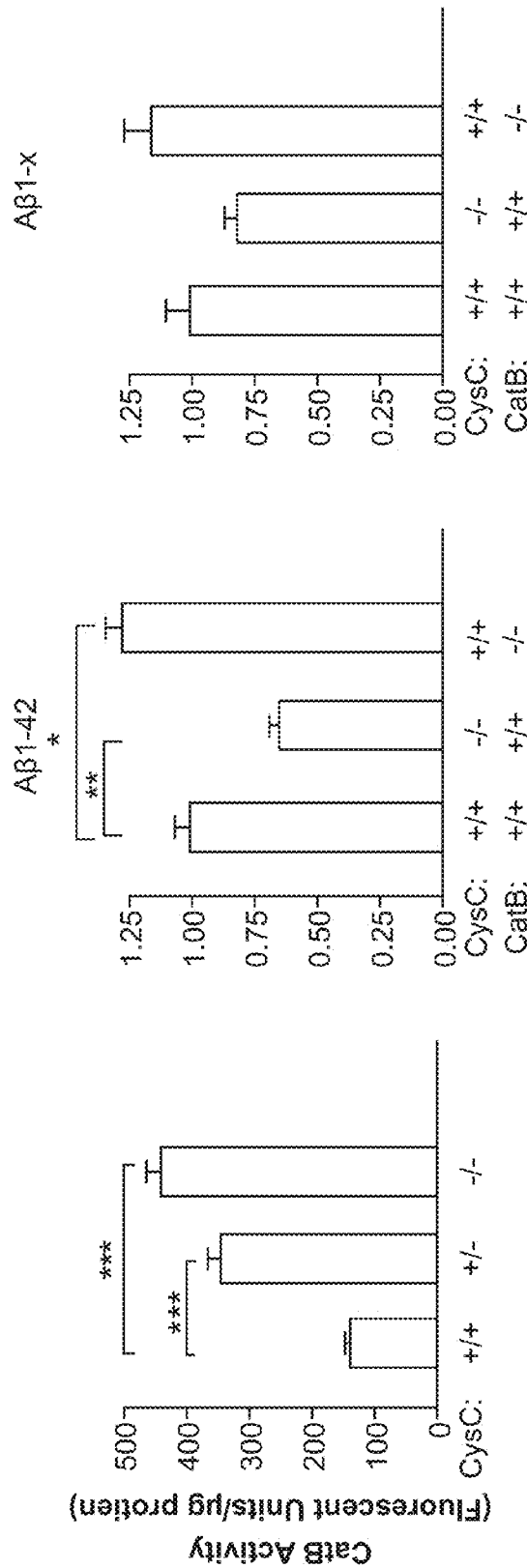

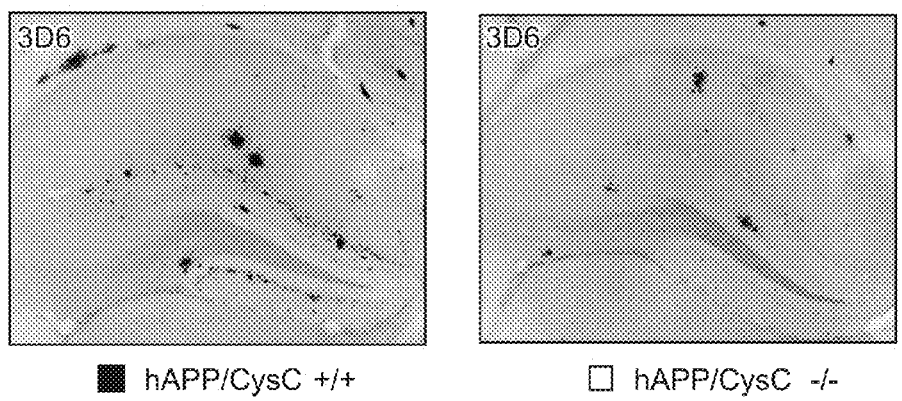
FIG. 3A
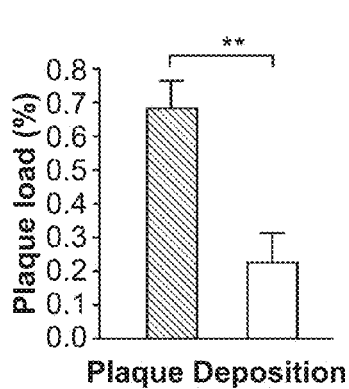 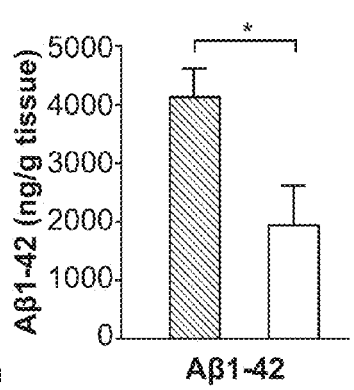 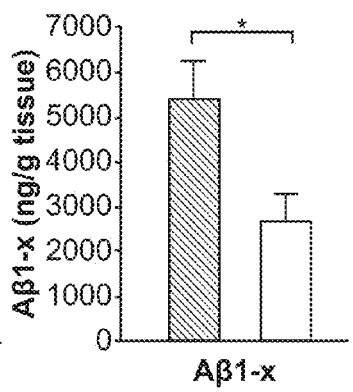
FIG. 3B     FIG. 3C     FIG. 3D

GenBank CAA36497

```
  1 magplrapll llailavala vspaagsspg kpprlvggpm dasveeegvr raldfavgey
 61 nkasndmyhs ralqvvrark qivagvnyfl dvelgrttct ktqpnldncp fhdqphlkrk
121 afcsfqiyav pwqgtmtlsk stcqda
```

FIG. 8A

GenBank X52255.1

```
  1 atggcgggc cctgcgcgc ccgctgctc ctgctggcca tcctggccgt ggccctggcc
 61 gtgagcccg cggccggctc cagtcccgg aagccgcgc gctgggg    aggcccatg
121 gacgtcagcg tggaggaga gggtgtgcgg cgtgcactgg actttgccgt cggcgagtac
181 aacaaagcca gcaacgacat gtaccacagc cgcgcgctgc agtggtgcg cgcccgcaag
241 cagatcgtag ctggggtgaa ctacttcttg gacgtggagc tggggccgaac cacgtgtacc
301 aagaccagc ccaacttgga caactgcccc ttccatgacc agccacatct gaaaaggaaa
361 gcattctgct ctttccagat ctacgctgtg ccttggcagg gcacaatgac cttgtcgaaa
421 tccacctgtc aggacgccta g
```

FIG. 8B

SEQUENCE LISTING

<160> NUMBER OF SEQ ID NOS: 14

<210> SEQ ID NO 1
<211> LENGTH: 146
<212> TYPE: PRT
<213> ORGANISM: Homo sapiens

<400> SEQUENCE: 1

Met Ala Gly Pro Leu Arg Ala Pro Leu Leu Leu Leu Ala Ile Leu Ala
1               5                   10                  15

Val Ala Leu Ala Val Ser Pro Ala Ala Gly Ser Ser Pro Gly Lys Pro
            20                  25                  30

Pro Arg Leu Val Gly Gly Pro Met Asp Ala Ser Val Glu Glu Glu Gly
        35                  40                  45

Val Arg Arg Ala Leu Asp Phe Ala Val Gly Glu Tyr Asn Lys Ala Ser
    50                  55                  60

Asn Asp Met Tyr His Ser Arg Ala Leu Gln Val Val Arg Ala Arg Lys
65                  70                  75                  80

Gln Ile Val Ala Gly Val Asn Tyr Phe Leu Asp Val Glu Leu Gly Arg
                85                  90                  95

```
Thr Thr Cys Thr Lys Thr Gln Pro Asn Leu Asp Asn Cys Pro Phe His
            100                 105                 110

Asp Gln Pro His Leu Lys Arg Lys Ala Phe Cys Ser Phe Gln Ile Tyr
        115                 120                 125

Ala Val Pro Trp Gln Gly Thr Met Thr Leu Ser Lys Ser Thr Cys Gln
130                 135                 140

Asp Ala
145

<210> SEQ ID NO 2
<211> LENGTH: 441
<212> TYPE: DNA
<213> ORGANISM: Homo sapiens

<400> SEQUENCE: 2
atggccgggc ccctgcgcgc cccgctgctc ctgctggcca tcctggccgt ggccctggcc      60
gtgagccccg cggccggctc cagtcccggc aagccgccgc gcctggtggg aggccccatg     120
gacgccagcg tggaggagga gggtgtgcgg cgtgcactgg actttgccgt cggcgagtac     180
aacaaagcca gcaacgacat gtaccacagc cgcgcgctgc aggtggtgcg cgcccgcaag     240
cagatcgtag ctggggtgaa ctacttcttg gacgtggagc tgggccgaac cacgtgtacc     300
aagacccagc ccaacttgga caactgcccc ttccatgacc agccacatct gaaaaggaaa     360
gcattctgct ctttccagat ctacgctgtg ccttggcagg gcacaatgac cttgtcgaaa     420
tccacctgtc aggacgccta g                                                441

<210> SEQ ID NO 3
<211> LENGTH: 50
<212> TYPE: PRT
<213> ORGANISM: Homo sapiens

<400> SEQUENCE: 3

Asn Lys Ala Ser Asn Asp Met Tyr His Ser Arg Ala Leu Gln Val Val
1               5                   10                  15

Arg Ala Arg Lys Gln Ile Val Ala Gly Val Asn Tyr Phe Leu Asp Val
            20                  25                  30

Glu Leu Gly Arg Thr Thr Cys Thr Lys Thr Gln Pro Asn Leu Asp Asn
        35                  40                  45

Cys Pro
    50

<210> SEQ ID NO 4
<211> LENGTH: 50
<212> TYPE: PRT
<213> ORGANISM: Mus musculus

<400> SEQUENCE: 4

Asn Lys Gly Ser Asn Asp Ala Tyr His Ser Arg Ala Ile Gln Val Val
1               5                   10                  15

Arg Ala Arg Lys Gln Leu Val Ala Gly Val Asn Tyr Phe Leu Asp Val
            20                  25                  30

Glu Met Gly Arg Thr Thr Cys Thr Lys Ser Gln Thr Asn Leu Thr Asp
        35                  40                  45

Cys Pro
    50

<210> SEQ ID NO 5
```

```
<211> LENGTH: 50
<212> TYPE: PRT
<213> ORGANISM: Rattus norvegicus

<400> SEQUENCE: 5

Asn Lys Gly Ser Asn Asp Ala Tyr His Ser Arg Ala Ile Gln Val Val
 1               5                  10                  15

Arg Ala Arg Lys Gln Leu Val Ala Gly Ile Asn Tyr Tyr Leu Asp Val
            20                  25                  30

Glu Met Gly Arg Thr Thr Cys Thr Lys Ser Gln Thr Asn Leu Thr Asn
        35                  40                  45

Cys Pro
    50

<210> SEQ ID NO 6
<211> LENGTH: 50
<212> TYPE: PRT
<213> ORGANISM: Oryctolagus cuniculus

<400> SEQUENCE: 6

Asn Lys Gly Ser Asn Asp Arg Tyr His Ser Arg Ala Leu Gln Val Val
 1               5                  10                  15

Arg Ala Arg Arg Gln Ile Val Ser Gly Val Lys Tyr Tyr Leu Asp Val
            20                  25                  30

Leu Ile Gly Arg Thr Thr Cys Thr Lys Thr Gln Thr Asn Leu Ala Asn
        35                  40                  45

Cys Pro
    50

<210> SEQ ID NO 7
<211> LENGTH: 52
<212> TYPE: DNA
<213> ORGANISM: Artificial Sequence
<220> FEATURE:
<223> OTHER INFORMATION: synthetic DNA

<400> SEQUENCE: 7
gtcccagaca aatttgactt tcaagagaag tcaaatttgt ctgggacttt tt          52

<210> SEQ ID NO 8
<211> LENGTH: 51
<212> TYPE: DNA
<213> ORGANISM: Artificial Sequence
<220> FEATURE:
<223> OTHER INFORMATION: synthetic DNA

<400> SEQUENCE: 8
gacccagccc aacttggatt tcaagagaat ccaagttggg ctgggtcttt t           51

<210> SEQ ID NO 9
<211> LENGTH: 47
<212> TYPE: DNA
<213> ORGANISM: Artificial Sequence
<220> FEATURE:
<223> OTHER INFORMATION: synthetic DNA

<400> SEQUENCE: 9
gacgccagcg tggaggagtt tcaagagaac tcctccacgc tggcgtc                47

<210> SEQ ID NO 10
<211> LENGTH: 47
<212> TYPE: DNA
<213> ORGANISM: Artificial Sequence
```

<220> FEATURE:
<223> OTHER INFORMATION: synthetic DNA

<400> SEQUENCE: 10
ccaacttgga caactgcctt tcaagagaag gcagttgtcc aagttgg    47

<210> SEQ ID NO 11
<211> LENGTH: 339
<212> TYPE: PRT
<213> ORGANISM: Homo sapiens

<400> SEQUENCE: 11

```
Met Trp Gln Leu Trp Ala Ser Leu Cys Cys Leu Leu Val Leu Ala Asn
  1               5                  10                  15

Ala Arg Ser Arg Pro Ser Phe His Pro Val Ser Asp Glu Leu Val Asn
             20                  25                  30

Tyr Val Asn Lys Arg Asn Thr Thr Trp Gln Ala Gly His Asn Phe Tyr
         35                  40                  45

Asn Val Asp Met Ser Tyr Leu Lys Arg Leu Cys Gly Thr Phe Leu Gly
     50                  55                  60

Gly Pro Lys Pro Pro Gln Arg Val Met Phe Thr Glu Asp Leu Lys Leu
 65                  70                  75                  80

Pro Ala Ser Phe Asp Ala Arg Glu Gln Trp Pro Gln Cys Pro Thr Ile
                 85                  90                  95

Lys Glu Ile Arg Asp Gln Gly Ser Cys Gly Ser Cys Trp Ala Phe Gly
            100                 105                 110

Ala Val Glu Ala Ile Ser Asp Arg Ile Cys Ile His Thr Asn Ala His
        115                 120                 125

Val Ser Val Glu Val Ser Ala Glu Asp Leu Leu Thr Cys Cys Gly Ser
    130                 135                 140

Met Cys Gly Asp Gly Cys Asn Gly Gly Tyr Pro Ala Glu Ala Trp Asn
145                 150                 155                 160

Phe Trp Thr Arg Lys Gly Leu Val Ser Gly Gly Leu Tyr Glu Ser His
                165                 170                 175

Val Gly Cys Arg Pro Tyr Ser Ile Pro Pro Cys Glu His His Val Asn
            180                 185                 190

Gly Ser Arg Pro Pro Cys Thr Gly Glu Gly Asp Thr Pro Lys Cys Ser
        195                 200                 205

Lys Ile Cys Glu Pro Gly Tyr Ser Pro Thr Tyr Lys Gln Asp Lys His
    210                 215                 220

Tyr Gly Tyr Asn Ser Tyr Ser Val Ser Asn Ser Glu Lys Asp Ile Met
225                 230                 235                 240

Ala Glu Ile Tyr Lys Asn Gly Pro Val Glu Gly Ala Phe Ser Val Tyr
                245                 250                 255

Ser Asp Phe Leu Leu Tyr Lys Ser Gly Val Tyr Gln His Val Thr Gly
            260                 265                 270

Glu Met Met Gly Gly His Ala Ile Arg Ile Leu Gly Trp Gly Val Glu
        275                 280                 285

Asn Gly Thr Pro Tyr Trp Leu Val Ala Asn Ser Trp Asn Thr Asp Trp
    290                 295                 300

Gly Asp Asn Gly Phe Phe Lys Ile Leu Arg Gly Gln Asp His Cys Gly
305                 310                 315                 320

Ile Glu Ser Glu Val Val Ala Gly Ile Pro Arg Thr Asp Gln Tyr Trp
                325                 330                 335

Glu Lys Ile
```

```
<210> SEQ ID NO 12
<211> LENGTH: 106
<212> TYPE: PRT
<213> ORGANISM: Artificial Sequence
<220> FEATURE:
<223> OTHER INFORMATION: variant cystatin c

<400> SEQUENCE: 12

Ser Ser Pro Gly Lys Pro Pro Arg Leu Val Gly Gly Pro Met Asp Ala
 1               5                  10                  15

Ser Val Glu Glu Glu Gly Val Arg Arg Ala Leu Asp Phe Ala Val Gly
             20                  25                  30

Glu Tyr Asn Lys Ala Ser Asn Asp Met Tyr His Ser Arg Ala Leu Gln
         35                  40                  45

Val Val Arg Ala Arg Leu Gly Arg Thr Thr Cys Thr Lys Thr Gln Pro
     50                  55                  60

Asn Leu Asp Asn Cys Pro Phe His Asp Gln Pro His Leu Lys Arg Lys
 65                  70                  75                  80

Ala Phe Cys Ser Phe Gln Ile Tyr Ala Val Pro Trp Gln Gly Thr Met
                 85                  90                  95

Thr Leu Ser Lys Ser Thr Cys Gln Asp Ala
            100                 105

<210> SEQ ID NO 13
<211> LENGTH: 89
<212> TYPE: PRT
<213> ORGANISM: Artificial Sequence
<220> FEATURE:
<223> OTHER INFORMATION: variant cystatin c

<400> SEQUENCE: 13

Ser Ser Pro Gly Lys Pro Pro Arg Leu Val Gly Gly Pro Met Asp Ala
 1               5                  10                  15

Ser Val Glu Glu Glu Gly Val Arg Arg Ala Leu Asp Phe Ala Val Gly
             20                  25                  30

Glu Tyr Asn Lys Ala Gly Arg Thr Thr Cys Thr Lys Thr Gln Pro Asn
         35                  40                  45

Leu Asp Asn Cys Pro Phe His Asp Gln Pro His Leu Lys Arg Lys Ala
 50                  55                  60

Phe Cys Ser Phe Gln Ile Tyr Ala Val Pro Trp Gln Gly Thr Met Thr
 65                  70                  75                  80

Leu Ser Lys Ser Thr Cys Gln Asp Ala
                 85

<210> SEQ ID NO 14
<211> LENGTH: 120
<212> TYPE: PRT
<213> ORGANISM: Homo sapiens

<400> SEQUENCE: 14

Ser Ser Pro Gly Lys Pro Pro Arg Leu Val Gly Gly Pro Met Asp Ala
 1               5                  10                  15

Ser Val Glu Glu Glu Gly Val Arg Arg Ala Leu Asp Phe Ala Val Gly
             20                  25                  30

Glu Tyr Asn Lys Ala Ser Asn Asp Met Tyr His Ser Arg Ala Leu Gln
         35                  40                  45

Val Val Arg Ala Arg Lys Gln Ile Val Ala Gly Val Asn Tyr Phe Leu
     50                  55                  60
```

```
Asp Val Glu Leu Gly Arg Thr Thr Cys Thr Lys Thr Gln Pro Asn Leu
65                  70              75                  80

Asp Asn Cys Pro Phe His Asp Gln Pro His Leu Lys Arg Lys Ala Phe
                85              90              95

Cys Ser Phe Gln Ile Tyr Ala Val Pro Trp Gln Gly Thr Met Thr Leu
            100             105             110

Ser Lys Ser Thr Cys Gln Asp Ala
        115             120
```

METHODS AND COMPOSITIONS FOR REDUCING AMYLOID BETA LEVELS

CROSS-REFERENCE

This application is a divisional of U.S. patent application Ser. No. 13/847,092, filed Mar. 19, 2013 now U.S. Pat. No. 8,691,519, which is a divisional of U.S. patent application Ser. No. 12/447,241, filed Oct. 22, 2009, now U.S. Pat. No. 8,420,613, which is a national stage filing under 35 U.S.C. §371 of PCT/US2007/024059, filed Nov. 15, 2011, which claims the benefit of U.S. Provisional Patent Application No. 60/859,326, filed Nov. 15, 2006, each of which applications is incorporated herein by reference in its entirety.

STATEMENT REGARDING FEDERALLY SPONSORED RESEARCH

This invention was made with Government support under contract AG024447 awarded by the National Institutes of Health. The Government has certain rights in this invention.

BACKGROUND

Alzheimer's disease (AD) is the most common cause of dementia, affecting tens of millions of individuals worldwide. Neuritic plaques are accumulations of aggregated amyloid beta (Aβ) peptides, including $A\beta_{1-40}$ and $A\beta_{1-42}$, derived from processing of amyloid precursor protein (APP) by β- and γ-secretases. The vast majority of autosomal familial AD (FAD)-linked mutations are associated with increased levels of $A\beta_{1-42}$, providing strong evidence that $A\beta_{1-42}$ plays a central role in AD pathogenesis. There are currently no effective therapies for arresting or reversing the impairment of cognitive function that characterizes AD. There is a need in the art for effective therapies for treating AD and related disorders.

Literature

Mueller-Steiner et al. (September 2006) *Neuron* 51:703-714; WO 2004/084830; Hook et al. (2005) *Biol. Chem.* 386:931-940; Hook (2006) *BioDrugs* 20:105-119; Hook (2006) *Biol. Chem.* 387:1429-1439; U.S. Patent Publication No. 2004/0248232; Cataldo and Nixon (1990) *Proc. Natl. Acad. Sci. USA* 87:3861-3865; Cataldo et al. (1997) *J. Neurosci.* 17:6142; Mackay et al. (1997) *Eur. J. Biochem.* 244:414-425.

SUMMARY OF THE INVENTION

The present invention provides methods for reducing the level of amyloid beta protein in a cell or tissue, the methods generally involving contacting the cell or tissue with an agent that reduces cystatin C levels and/or activity. The present invention provides methods for treating Alzheimer's disease (AD), and methods for treating cerebral angiopathy, in an individual, the methods generally involving administering to an individual having AD a therapeutically effective amount of an agent that reduces cystatin C levels and/or activity. The present invention further provides methods for identifying an agent that reduces cystatin C levels and/or activity.

BRIEF DESCRIPTION OF THE DRAWINGS

FIGS. 2A-C depict CatB activity, $A\beta_{1-42}$, and $A\beta_{1-x}$ levels in CysC ablated and wild-type mice.

FIGS. 3A-D depict the effects of CysC on plaque loads and Aβ levels in hAPP mice.

FIG. 8A depicts an amino acid sequence of human CysC (SEQ ID NO:1); and FIG. 8B depicts a nucleotide sequence encoding human CysC (SEQ ID NO:2).

DEFINITIONS

Figure 1A:
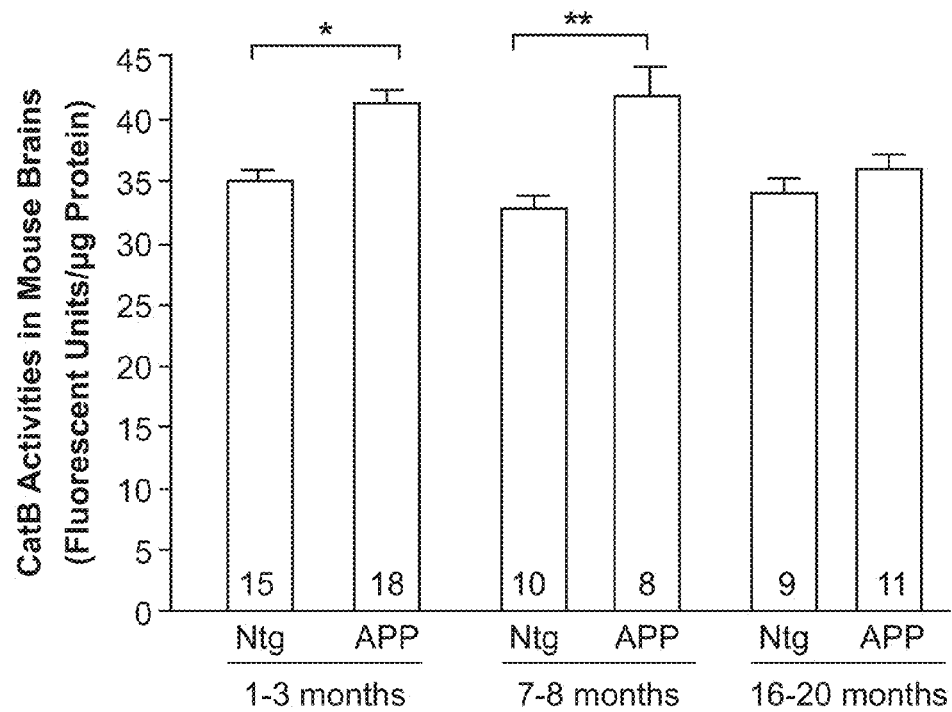
FIGS. 1A-C depict cathepsin B (CatB) activity and cystatin C (CysC) levels in wildtype) CysC+/+), cysC (cysC+/−) heterozygoutes, and cysC null mice (cysC−/−).

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," "host," and "patient," used interchangeably herein, refer to a mammal, including, but not limited to, murines, simians, humans, mammalian farm animals, mammalian sport animals, and mammalian pets.

A "therapeutically effective amount" or "efficacious amount" means the amount of a compound that, when administered to a mammal or other subject for treating a disease, is sufficient to effect such treatment for the disease. The "therapeutically effective amount" will vary depending on the compound, the disease and its severity and the age, weight, etc., of the subject to be treated.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides or polypeptides. The term "biological sample" encompasses a clinical sample, and also includes cells in culture, cell supernatants, cell lysates, serum, plasma, biological fluid, and tissue samples. In some embodiments, a biological sample will include cells (e.g., neuronal cells; glial cells).

As used herein, the phrase "pharmaceutically acceptable carrier" refers to a carrier medium that does not interfere with the effectiveness of the biological activity of the active ingredient. Said carrier medium is essentially chemically inert and nontoxic.

As used herein, the phrase "pharmaceutically acceptable" means approved by a regulatory agency of the Federal government or a state government, or listed in the U.S. Pharmacopeia or other generally recognized pharmacopeia for use in animals, and more particularly for use in humans.

As used herein, the term "carrier" refers to a diluent, adjuvant, excipient, or vehicle with which the therapeutic is administered. Such carriers can be sterile liquids, such as saline solutions in water, or oils, including those of petroleum, animal, vegetable or synthetic origin, such as peanut oil, soybean oil, mineral oil, sesame oil and the like. A saline solution is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The carrier, if desired, can also contain minor amounts of wetting or emulsifying agents, or pH buffering agents. These pharmaceutical compositions can take the form of solutions, suspensions, emulsion, tablets, pills, capsules, powders, sustained-release formulations and the like. The composition can be formulated as a suppository, with traditional binders and carriers such as triglycerides. Examples of suitable pharmaceutical carriers are described in *Remington's Pharmaceutical Sciences* by E. W. Martin. Examples of suitable pharmaceutical carriers are a variety of cationic polyamines and lipids, including, but not limited to N-(1(2,3-dioleyloxy)propyl)-N,N,N-trimethylammonium chloride (DOTMA) and dioleysylphosphotidylethanolamine (DOPE). Liposomes are suitable carriers for gene therapy uses of the invention. Such pharmaceutical compositions should contain a therapeutically effective amount of the compound, together with a suitable amount of carrier so as to provide the form for proper administration to the subject. The formulation should suit the mode of administration.

The terms "polynucleotide" and "nucleic acid," used interchangeably herein, refer to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence similarity can be determined in a number of different manners. To determine sequence identity, sequences can be aligned using the methods and computer programs, including BLAST, available over the world wide web at ncbi.nlm.nih.gov/BLAST. See, e.g., Altschul et al. (1990), *J. Mol. Biol.* 215:403-10. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See *Meth. Mol. Biol.* 70: 173-187 (1997). Also, the GAP program using the Needleman and Wunsch alignment method can be utilized to align sequences. See *J. Mol. Biol.* 48: 443-453 (1970).

A nucleic acid is "hybridizable" to another nucleic acid, such as a cDNA, genomic DNA, or RNA, when a single stranded form of the nucleic acid can anneal to the other nucleic acid under the appropriate conditions of temperature and solution ionic strength. Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein; and Sambrook, J. and Russell, W., Molecular Cloning: A Laboratory Manual, Third Edition, Cold Spring Harbor Laboratory Press, Cold Spring Harbor (2001). The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Hybridization conditions and post-hybridization washes are useful to obtain the desired determine stringency conditions of the hybridization. One set of illustrative post-hybridization washes is a series of washes starting with 6×SSC (where SSC is 0.15 M NaCl and 15 mM citrate buffer), 0.5% SDS at room temperature for 15 minutes, then repeated with 2×SSC, 0.5% SDS at 45° C. for 30 minutes, and then repeated twice with 0.2×SSC, 0.5% SDS at 50° C. for 30 minutes. Other stringent conditions are obtained by using higher temperatures in which the washes are identical to those above except for the temperature of the final two 30 minute washes in 0.2×SSC, 0.5% SDS, which is increased to 60° C. Another set of highly stringent conditions uses two final washes in 0.1×SSC, 0.1% SDS at 65° C. Another example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH 7.6), 5×Denhardt's solution, 10% dextran sulfate, and 20 μg/ml denatured, sheared salmon sperm DNA, followed by washing the filters in 0.1× SSC at about 65° C. Stringent hybridization conditions and post-hybridization wash conditions are hybridization conditions and post-hybridization wash conditions that are at least as stringent as the above representative conditions.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of the melting temperature (Tm) for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). Typically, the length for a hybridizable nucleic acid is at least about 10 nucleotides. Illustrative minimum lengths for a hybridizable nucleic acid are: at least about 15 nucleotides; at least about 20 nucleotides; and at least about 30 nucleotides. Furthermore, the skilled artisan will recognize that the temperature and wash solution salt concentration may be adjusted as necessary according to factors such as length of the probe.

As used herein the term "isolated" is meant to describe a polynucleotide, a polypeptide, or a cell that is in an environment different from that in which the polynucleotide, the polypeptide, or the cell naturally occurs. An isolated genetically modified host cell may be present in a mixed population of genetically modified host cells.

As used herein, the term "exogenous nucleic acid" refers to a nucleic acid that is not normally or naturally found in and/or produced by a given bacterium, organism, or cell in nature. As used herein, the term "endogenous nucleic acid" refers to a nucleic acid that is normally found in and/or produced by a given bacterium, organism, or cell in nature.

"Recombinant," as used herein, means that a particular nucleic acid (DNA or RNA) is the product of various combinations of cloning, restriction, and/or ligation steps resulting in a construct having a structural coding or non-coding sequence distinguishable from endogenous nucleic acids found in natural systems.

Thus, e.g., the term "recombinant" polynucleotide or "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques.

By "construct" or "vector" is meant a recombinant nucleic acid, generally recombinant DNA, which has been generated for the purpose of the expression and/or propagation of a specific nucleotide sequence(s), or is to be used in the construction of other recombinant nucleotide sequences.

"Operably linked" refers to a juxtaposition wherein the components so described are in a relationship permitting them to function in their intended manner. For instance, a promoter is operably linked to a coding sequence if the promoter affects its transcription or expression.

The term "transformation" is used interchangeably herein with "genetic modification" and refers to a permanent or transient genetic change induced in a cell following introduction of new nucleic acid (i.e., DNA exogenous to the cell). Genetic change ("modification") can be accomplished either by incorporation of the new DNA into the genome of the host cell, or by transient or stable maintenance of the new DNA as an episomal element.

A "host cell," as used herein, denotes an in vivo or in vitro eukaryotic cell, a prokaryotic cell, or a cell from a multicellular organism (e.g., a cell line) cultured as a unicellular entity, which eukaryotic or prokaryotic cells can be, or have been, used as recipients for a nucleic acid, and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector.

As used herein, the term "neurons" or "neuronal cells" includes any cell population that includes neurons of any type, including, but not limited to, primary cultures of brain cells that contain neurons, isolated cell cultures comprising primary neuronal cells, neuronal precursor cells, tissue culture cells that are used as models of neurons, and mixtures thereof.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a cathepsin B polypeptide" includes a plurality of such polypeptide and reference to "the active agent" includes reference to one or more active agents and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present invention provides methods of reducing the level of amyloid beta protein (e.g., $A\beta_{1-42}$) in a cell or a tissue. The methods generally involve contacting the cell or tissue with an agent that selectively reduces cystatin C levels and/or activity in the cell or tissue. Reduction of cystatin C levels and/or activity results in a reduced level of amyloid beta protein in the cell or tissue. The methods are useful for treating Alzheimer's disease (AD) in an individual. Thus, the present invention further provides methods of treating AD in an individual, the methods generally involving administering to an individual having AD a therapeutically effective amount of an agent that selectively reduces cystatin C levels and/or activity in the cell or tissue. The methods are also useful for treating cerebral angiopathy in an individual.

Methods for Reducing Amyloid Beta Levels

The present invention provides methods of reducing the level of amyloid beta protein (e.g., $A\beta_{1-42}$) in a cell or a tissue. The methods generally involve contacting the cell or tissue with an agent that selectively reduces cystatin C levels and/or activity in the cell or tissue. Reduction of cystatin C levels and/or activity results in a reduced level of amyloid beta protein in the cell or tissue.

Suitable agents (also referred to herein as "active agents") that selectively reduce cystatin C levels and/or activity include, but are not limited to, an interfering nucleic acid that reduces the level of cystatin C expression in a cell or tissue; a dominant negative mutant of cystatin C; a small molecule inhibitor of cystatin C that interferes with its interaction with cysteine proteases; an antibody that specifically binds cystatin C and reduces binding of cystatin C to cysteine proteases; an antibody that specifically binds cystatin C and reduces levels of cystatin C in the brain; an antibody that specifically binds cystatin C and reduces binding of cystatin C to cathepsin B; and a peptide that reduces binding of cystatin C to cysteine proteases, including cathepsin B. In some embodiments, an active agent is an agent that reduces cystatin C-mediated inhibition of a cysteine protease, such as cathepsin B.

Whether a subject method is effective in reducing $A\beta$ levels can be determined in an animal model by examining tissue histochemically or biochemically. In some embodiments, a reduction in $A\beta$ levels leads to an increase in cognitive function and/or an improvement in various behavioral tests. Behavioral tests designed to assess learning and memory deficits can be employed. An example of such as test is the Morris Water maze (Morris *Learn Motivat* 12:239-260 (1981)). In this procedure, the animal is placed in a circular pool filled with water, with an escape platform submerged just below the surface of the water. A visible marker is placed on the platform so that the animal can find it by navigating toward a proximal visual cue. Alternatively, a more complex form of the test in which there are no formal cues to mark the platform's location will be given to the animals. In this form, the animal must learn the platform's location relative to distal visual cues. Alternatively, or in addition, memory and learning deficits can be studied using a 3 runway panel for working memory impairment (attempts to pass through two incorrect panels of the three panel-gates at four choice points) (Ohno et al. *Pharmacol Biochem Behav* 57:257-261 (1997)).

In some embodiments, a reduction in $A\beta$ levels reduces neuronal cell damage. Rodent models of neuronal damage, for example neuronal damage caused by cerebral ischemia, may be examined to determine the efficacy of a subject method. Rodent models of cerebral ischemia, both global ischemia and focal ischemia, are useful for studying mechanisms controlling the occurrence of cerebral ischemia and potential therapeutic strategies for treatment of injury caused by ischemic events. Animal models of global ischemia, which is usually transient, have widely affected brain areas but typically give rise to neuronal alterations in selectively vulnerable brain regions. Examples of such models include, but are not limited to, the two vessel occlusion model of forebrain ischemia, the four vessel occlusion model of forebrain ischemia, and ischemia models involving elevated cerebrospinal fluid pressure. See Ginsberg and Busto, *Stroke,* 20:1627-1642 (1989), which is herein incorporated by reference. Models of focal ischemia may mimic ischemic stroke injury, and typically give rise to localized brain infarction. Examples of models of focal ischemia include, but are not limited to, middle cerebral artery occlusion, photochemically induced focal cerebral thrombosis, blood clot embolization, microsphere embolization and the like. See McAuley, *Cerebrovasc. Brain Metab. Review,* 7:153-180 (1995) which is herein incorporated by reference.

Interfering Nucleic Acid

In some embodiments, a subject method involves contacting a cell or tissue, or administering to an individual, an interfering nucleic acid that reduces the level of cystatin C expression. In some embodiments, a subject method involves contacting a cell or tissue, or administering to an individual, a nucleic acid comprising a nucleotide sequence that encodes an interfering nucleic acid.

The terms "short interfering nucleic acid," "siNA," "short interfering RNA," "siRNA," "short interfering nucleic acid molecule," "short interfering oligonucleotide molecule," and "chemically-modified short interfering nucleic acid molecule" as used herein refer to any nucleic acid molecule capable of inhibiting or down regulating gene expression, for example by mediating RNA interference "RNAi" or gene silencing in a sequence-specific manner. Design of RNAi molecules, when given a target gene, is routine in the art. See also US 2005/0282188 (which is incorporated herein by reference) as well as references cited therein. See, e.g., Pushparaj et al. Clin Exp Pharmacol Physiol. 2006 May-June; 33(5-6):504-10; Lutzelberger et al. Handb Exp Pharmacol. 2006; (173):243-59; Aronin et al. Gene Ther. 2006 March; 13(6):509-16; Xie et al. Drug Discov Today. 2006 January; 11(1-2):67-73; Grunweller et al. Curr Med Chem. 2005; 12(26):3143-61; and Pekaraik et al. Brain Res Bull. 2005 Dec. 15; 68(1-2):115-20. Epub 2005 Sep. 9.

Methods for design and production of siRNAs to a desired target are known in the art, and their application to cystatin C genes for the purposes disclosed herein will be readily apparent to the ordinarily skilled artisan, as are methods of production of siRNAs having modifications (e.g., chemical modifications) to provide for, e.g., enhanced stability, bioavailability, and other properties to enhance use as therapeutics. In addition, methods for formulation and delivery of siRNAs to a subject are also well known in the art. See, e.g., US 2005/0282188; US 2005/0239731; US 2005/0234232; US 2005/0176018; US 2005/0059817; US 2005/0020525; US 2004/0192626; US 2003/0073640; US 2002/0150936;

US 2002/0142980; and US2002/0120129, each of which are incorporated herein by reference.

Publicly available tools to facilitate design of siRNAs are available in the art. See, e.g., DEQOR: Design and Quality Control of RNAi (available on the internet at cluster-1.mpi-cbg.de/Deqor/deqor.html). See also, Henschel et al. Nucleic Acids Res. 2004 Jul. 1; 32(Web Server issue):W113-20. DEQOR is a web-based program which uses a scoring system based on state-of-the-art parameters for siRNA design to evaluate the inhibitory potency of siRNAs. DEQOR, therefore, can help to predict (i) regions in a gene that show high silencing capacity based on the base pair composition and (ii) siRNAs with high silencing potential for chemical synthesis. In addition, each siRNA arising from the input query is evaluated for possible cross-silencing activities by performing BLAST searches against the transcriptome or genome of a selected organism. DEQOR can therefore predict the probability that an mRNA fragment will cross-react with other genes in the cell and helps researchers to design experiments to test the specificity of siRNAs or chemically designed siRNAs.

siNA molecules can be of any of a variety of forms. For example the siNA can be a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof siNA can also be assembled from two separate oligonucleotides, where one strand is the sense strand and the other is the antisense strand, wherein the antisense and sense strands are self-complementary. In this embodiment, each strand comprises nucleotide sequence that is complementary to nucleotide sequence in the other strand; such as where the antisense strand and sense strand form a duplex or double stranded structure, for example wherein the double stranded region is about 15 to about 30, e.g., about 15, 16, 17, 18, 19, 20, 21, 22, 23, 24, 25, 26, 27, 28, 29 or 30 base pairs; the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof (e.g., about 15 to about 25 or more nucleotides of the siNA molecule are complementary to the target nucleic acid or a portion thereof).

Alternatively, the siNA can be assembled from a single oligonucleotide, where the self-complementary sense and antisense regions of the siNA are linked by a nucleic acid-based or non-nucleic acid-based linker(s). The siNA can be a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof.

The siNA can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siNA molecule capable of mediating RNAi. The siNA can also comprise a single stranded polynucleotide having nucleotide sequence complementary to nucleotide sequence in a target nucleic acid molecule or a portion thereof (e.g., where such siNA molecule does not require the presence within the siNA molecule of nucleotide sequence corresponding to the target nucleic acid sequence or a portion thereof), wherein the single stranded polynucleotide can further comprise a terminal phosphate group, such as a 5'-phosphate (see for example Martinez et al., 2002, Cell., 110, 563-574 and Schwarz et al., 2002, Molecular Cell, 10, 537-568), or 5',3'-diphosphate.

In certain embodiments, the siNA molecule contains separate sense and antisense sequences or regions, wherein the sense and antisense regions are covalently linked by nucleotide or non-nucleotide linkers molecules as is known in the art, or are alternately non-covalently linked by ionic interactions, hydrogen bonding, van der Waals interactions, hydrophobic interactions, and/or stacking interactions. In certain embodiments, the siNA molecules comprise nucleotide sequence that is complementary to nucleotide sequence of a target gene. In another embodiment, the siNA molecule interacts with nucleotide sequence of a target gene in a manner that causes inhibition of expression of the target gene.

As used herein, siNA molecules need not be limited to those molecules containing only RNA, but further encompasses chemically-modified nucleotides and non-nucleotides. In certain embodiments, the short interfering nucleic acid molecules of the invention lack 2'-hydroxy (2'-OH) containing nucleotides. siNAs do not necessarily require the presence of nucleotides having a 2'-hydroxy group for mediating RNAi and as such, siNA molecules of the invention optionally do not include any ribonucleotides (e.g., nucleotides having a 2'-OH group). Such siNA molecules that do not require the presence of ribonucleotides within the siNA molecule to support RNAi can however have an attached linker or linkers or other attached or associated groups, moieties, or chains containing one or more nucleotides with 2'-OH groups. Optionally, siNA molecules can comprise ribonucleotides at about 5, 10, 20, 30, 40, or 50% of the nucleotide positions. The modified short interfering nucleic acid molecules of the invention can also be referred to as short interfering modified oligonucleotides "siMON."

As used herein, the term siNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), and others. In some embodiments, an siNA is an siRNA. In some embodiments, a DNA comprising a nucleotide sequence encoding an siRNA is used. In addition, as used herein, the term RNAi is meant to be equivalent to other terms used to describe sequence specific RNA interference, such as post transcriptional gene silencing, translational inhibition, or epigenetics. For example, siNA molecules of the invention can be used to epigenetically silence a target gene at the post-transcriptional level or the pre-transcriptional level. In a non-limiting example, epigenetic regulation of gene expression by siNA molecules of the invention can result from siNA mediated modification of chromatin structure or methylation pattern to alter gene expression (see, for example, Verdel et al., 2004, Science, 303, 672-676; Pal-Bhadra et al., 2004, Science, 303, 669-672; Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237).

siNA (e.g., siRNA) molecules contemplated herein can comprise a duplex forming oligonucleotide (DFO) see, e.g., WO 05/019453; and US 2005/0233329, which are incorporated herein by reference). siNA molecules also contemplated herein include multifunctional siNA, (see, e.g., WO 05/019453 and US 2004/0249178). The multifunctional siNA can comprise sequence targeting, for example, two regions of FBXW8, CUL1, and/or CUL7.

siNA (e.g., siRNA) molecules contemplated herein can comprise an asymmetric hairpin or asymmetric duplex. By "asymmetric hairpin" as used herein is meant a linear siNA molecule comprising an antisense region, a loop portion that can comprise nucleotides or non-nucleotides, and a sense region that comprises fewer nucleotides than the antisense region to the extent that the sense region has enough complementary nucleotides to base pair with the antisense region and form a duplex with loop. For example, an asymmetric hairpin siNA molecule can comprise an antisense region having length sufficient to mediate RNAi in a cell or in vitro system (e.g. about 15 to about 30, or about 15, 16, 17, 18, 19, 20, 21, 22, 23, 24, 25, 26, 27, 28, 29, or 30 nucleotides) and a loop region comprising about 4 to about 12 (e.g., about 4, 5, 6, 7, 8, 9, 10, 11, or 12) nucleotides, and a sense region having about 3 to about 25 (e.g., about 3, 4, 5, 6, 7, 8, 9, 10, 11, 12, 13, 14, 15, 16, 17, 18, 19, 20, 21, 22, 23, 24, or 25) nucleotides that are complementary to the antisense region. The asymmetric hairpin siNA molecule can also comprise a 5'-terminal phosphate group that can be chemically modified. The loop portion of the asymmetric hairpin siNA molecule can comprise nucleotides, non-nucleotides, linker molecules, or conjugate molecules as described herein.

By "asymmetric duplex" as used herein is meant a siNA molecule having two separate strands comprising a sense region and an antisense region, wherein the sense region comprises fewer nucleotides than the antisense region to the extent that the sense region has enough complementary nucleotides to base pair with the antisense region and form a duplex. For example, an asymmetric duplex siNA molecule of the invention can comprise an antisense region having length sufficient to mediate RNAi in a cell or in vitro system (e.g. about 15 to about 30, or about 15, 16, 17, 18, 19, 20, 21, 22, 23, 24, 25, 26, 27, 28, 29, or 30 nucleotides) and a sense region having about 3 to about 25 (e.g., about 3, 4, 5, 6, 7, 8, 9, 10, 11, 12, 13, 14, 15, 16, 17, 18, 19, 20, 21, 22, 23, 24, or 25) nucleotides that are complementary to the antisense region.

Stability and/or half-life of siRNAs can be improved through chemically synthesizing nucleic acid molecules with modifications (base, sugar and/or phosphate) can prevent their degradation by serum ribonucleases, which can increase their potency (see e.g., Eckstein et al., International Publication No. WO 92/07065; Perrault et al., 1990 Nature 344, 565; Pieken et al., 1991, Science 253, 314; Usman and Cedergren, 1992, Trends in Biochem. Sci. 17, 334; Usman et al., International Publication No. WO 93/15187; and Rossi et al., International Publication No. WO 91/03162; Sproat, U.S. Pat. No. 5,334,711; Gold et al., U.S. Pat. No. 6,300,074; and Burgin et al., supra; all of which are incorporated by reference herein, describing various chemical modifications that can be made to the base, phosphate and/or sugar moieties of the nucleic acid molecules described herein. Modifications that enhance their efficacy in cells, and removal of bases from nucleic acid molecules to shorten oligonucleotide synthesis times and reduce chemical requirements are desired.

For example, oligonucleotides are modified to enhance stability and/or enhance biological activity by modification with nuclease resistant groups, for example, 2'-amino, 2'-C-allyl, 2'-fluoro, 2'-O-methyl, 2'-O-allyl, 2'-H, nucleotide base modifications (for a review see Usman and Cedergren, 1992, TIBS. 17, 34; Usman et al., 1994, Nucleic Acids Symp. Ser. 31, 163; Burgin et al., 1996, Biochemistry, 35, 14090). Sugar modification of nucleic acid molecules have been extensively described in the art (see Eckstein et al., International Publication PCT No. WO 92/07065; Perrault et al. Nature, 1990, 344, 565-568; Pieken et al. Science, 1991, 253, 314-317; Usman and Cedergren, Trends in Biochem. Sci., 1992, 17, 334-339; Usman et al. International Publication PCT No. WO 93/15187; Sproat, U.S. Pat. No. 5,334,711 and Beigelman et al., 1995, J. Biol. Chem., 270, 25702; Beigelman et al., International PCT publication No. WO 97/26270; Beigelman et al., U.S. Pat. No. 5,716,824; Usman et al., U.S. Pat. No. 5,627,053; Woolf et al., International PCT Publication No. WO 98/13526; Thompson et al., U.S. Ser. No. 60/082,404 which was filed on Apr. 20, 1998; Karpeisky et al., 1998, Tetrahedron Lett., 39, 1131; Eamshaw and Gait, 1998, Biopolymers (Nucleic Acid Sciences), 48, 39-55; Verma and Eckstein, 1998, Annu. Rev. Biochem., 67, 99-134; and Burlina et al., 1997, Bioorg. Med. Chem., 5, 1999-2010; each of which are hereby incorporated in their totality by reference herein). In view of such teachings, similar modifications can be used as described herein to modify the siNA nucleic acid molecules of disclosed herein so long as the ability of siNA to promote RNAi is cells is not significantly inhibited.

Short interfering nucleic acid (siNA) molecules (e.g., siRNA) having chemical modifications that maintain or enhance activity are contemplated herein. Such a nucleic acid is also generally more resistant to nucleases than an unmodified nucleic acid. Accordingly, the in vitro and/or in vivo activity should not be significantly lowered. Nucleic acid molecules delivered exogenously are generally selected to be stable within cells at least for a period sufficient for transcription and/or translation of the target RNA to occur and to provide for modulation of production of the encoded mRNA and/or polypeptide so as to facilitate reduction of the level of the target gene product.

Production of RNA and DNA molecules can be accomplished synthetically and can provide for introduction of nucleotide modifications to provide for enhanced nuclease stability. (see, e.g., Wincott et al., 1995, Nucleic Acids Res. 23, 2677; Caruthers et al., 1992, Methods in Enzymology 211, 3-19, incorporated by reference herein. In one embodiment, nucleic acid molecules of the invention include one or more (e.g., about 1, 2, 3, 4, 5, 6, 7, 8, 9, 10, or more) G-clamp nucleotides, which are modified cytosine analogs which confer the ability to hydrogen bond both Watson-Crick and Hoogsteen faces of a complementary guanine within a duplex, and can provide for enhanced affinity and specificity to nucleic acid targets (see, e.g., Lin et al. 1998, J. Am. Chem. Soc., 120, 8531-8532). In another example, nucleic acid molecules can include one or more (e.g., about 1, 2, 3, 4, 5, 6, 7, 8, 9, 10, or more) LNA "locked nucleic acid" nucleotides such as a 2',4'-C methylene bicyclo nucleotide (see, e.g., Wengel et al., WO 00/66604 and WO 99/14226).

siNA molecules can be provided as conjugates and/or complexes, e.g., to facilitate delivery of siNA molecules into a cell. Exemplary conjugates and/or complexes includes those composed of an siNA and a small molecule, lipid, cholesterol, phospholipid, nucleoside, antibody, toxin, negatively charged polymer (e.g., protein, peptide, hormone, carbohydrate, polyethylene glycol, or polyamine). In general, the transporters described are designed to be used either individually or as part of a multi-component system, with or without degradable linkers. These compounds can improve delivery and/or localization of nucleic acid molecules into cells in the presence or absence of serum (see, e.g., U.S. Pat. No. 5,854,038). Conjugates of the molecules described herein can be attached to biologically active molecules via linkers that are biodegradable, such as biodegradable nucleic acid linker molecules.

Non-limiting examples of nucleotide sequences encoding siRNA include, e.g.,

```
                                            (SEQ ID NO: 7)
5'-gtcccagacaaatttgactttcaagagaagtcaaatttgtctgggac ttttt-3';

(SEQ ID NO: 8)
5'-gacccagcccaacttggatttcaagagaatccaagttgggctgggtc tttt-3';

(SEQ ID NO: 9)
5'-gacgccagcgtggaggagtttcaagagaactcctccacgctggcgt c-3';
and (SEQ ID NO: 10)
5'-ccaacttgga caactgcctttcaagagaaggcagttgtccaagtt gg-3'.
```

The underlined nucleotides correspond to a loop; and bold nucleotides are palindromic sequences that include 18 nucleotides corresponding to mouse (SEQ ID NO:7) or human (SEQ ID NOs:8-10) cystatin C. In some embodiments, a nucleic acid comprising a nucleotide sequence encoding an siRNA is administered to an individual in need thereof.

Variants of Cystatin C (CysC)

In some embodiments, an active agent is a dominant negative variant of cystatin C.

The structure of cystatin C is known. See, e.g., Hall et al. (1995) *J. Biol. Chem.* 270:5115-5121; Janowski et al. (2001) *Nature Structural Biol.* 8:316-320; and Pol and Bjork (2001) *Protein Sci.* 10:1729-1738. Cystatin C interacts reversibly with its target protease by contributions from a wedge-shaped binding region comprising two loop-forming inhibitor segments; and a binding region corresponding to the N-terminal segment of the inhibitor. An amino acid sequence of human CysC is provided under GenBank Accession No. CAA36497; and depicted in FIG. 8A (SEQ ID NO:1). In FIG. 8A, the signal peptide is underlined; and "Arg-8" and "Leu-9" are shown in bold. A nucleotide sequence encoding human CysC is provided under GenBank Accession No. X52255.1; and depicted in FIG. 8B (SEQ ID NO:2).

In some embodiments, a variant cystatin C polypeptide suitable for use in a subject method lacks all or a portion of the protease inhibitory domain of CysC. For example, in some embodiments, a suitable CysC variant is one in which the biological activity of the conserved cysteine proteinase inhibitor motif is reduced or abolished. For example, in some embodiments, a suitable CysC variant lacks all or a portion of amino acids 80 through 93 of the amino acid sequence depicted in FIG. 8A. In other embodiments, a suitable CysC variant lacks all or a portion of amino acids 64 through 94 of the amino acid sequence depicted in FIG. 8A.

For example, in some embodiments, a suitable CysC variant comprises an amino acid sequence having at least about 75%, at least about 80%, at least about 85%, at least about 90%, at least about 95%, at least about 98%, at least about 99%, or more, amino acid sequence identity with the amino acid sequence set forth in SEQ ID NO:12. In other embodiments, a suitable CysC variant comprises an amino acid sequence having at least about 75%, at least about 80%, at least about 85%, at least about 90%, at least about 95%, at least about 98%, at least about 99%, or more, amino acid sequence identity with the amino acid sequence set forth in SEQ ID NO:13.

In some embodiments, one or more of Arg-8 and Leu-9 is mutated. For example, in some embodiments, one or more of Arg-8 and Leu-9 is mutated to a Gly residue. Thus, e.g., in some embodiments, a suitable CysC variant comprises an amino acid sequence having at least about 75%, at least about 80%, at least about 85%, at least about 90%, at least about 95%, at least about 98%, at least about 99%, or more, amino acid sequence identity with the amino acid sequence set forth in SEQ ID NO:12, 13, or 14, where the Arg-8 is substituted with a Gly. In other embodiments, a suitable CysC variant comprises an amino acid sequence having at least about 75%, at least about 80%, at least about 85%, at least about 90%, at least about 95%, at least about 98%, at least about 99%, or more, amino acid sequence identity with the amino acid sequence set forth in SEQ ID NO:12, 13, or 14, where the Leu-9 is substituted with Gly. In other embodiments, a suitable CysC variant comprises an amino acid sequence having at least about 75%, at least about 80%, at least about 85%, at least about 90%, at least about 95%, at least about 98%, at least about 99%, or more, amino acid sequence identity with the amino acid sequence set forth in SEQ ID NO:12, 13, or 14, where the Arg-8 is substituted with a Gly, and the Leu-9 is substituted with a Gly.

In some embodiments, a suitable CysC variant exhibits reduced binding affinity for cysteine proteases compared to the affinity of wild-type CysC for cysteine proteases. For example, a suitable variant CysC polypeptide exhibits a binding affinity for CatB cysteine protease activity that is from about 10% to about 20%, from about 20% to about 30%, from about 30% to about 40%, from about 40% to about 50%, from about 50% to about 60%, from about 60% to about 70%, from about 70% to about 80%, or from about 80% to about 90% less than the binding affinity of wild-type CysC for CatB. Thus, e.g., a suitable variant CysC polypeptide exhibits an at least about 10%, at least about 20%, at least about 30%, at least about 40%, at least about 50%, at least about 60%, at least about 70%, at least about 80%, or at least about 90%, or greater, reduction in binding affinity to CatB. In some embodiments, suitable CysC variant exhibits reduced inhibition of cathepsin B cysteine protease activity. For example, a suitable CysC variant has a reduction of at least about 10%, at least about 20%, at least about 30%, at least about 40%, at least about 50%, at least about 60%, at least about 70%, at least about 80%, or at least about 90%, or more, in inhibitory activity toward cysteine proteases. In some embodiments, the CysC variant has reduced binding affinity for cysteine proteases, and retains other biological functions of CysC.

A CysC variant can be administered together with a suitable pharmaceutically acceptable carrier or excipient. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., 7th ed., Lippincott, Williams, & Wilkins; and Handbook of Pharmaceutical Excipients (2000) A. H. Kibbe et al., eds., 3rd ed. Amer. Pharmaceutical Assoc. The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

The CysC variant polypeptide is prepared for storage or administration by mixing the CysC variant polypeptide having the desired degree of purity with physiologically acceptable carriers, excipients, or stabilizers. Such materials are non-toxic to recipients at the dosages and concentrations employed. If the CysC variant polypeptide is water soluble, it may be formulated in a buffer such as phosphate or other organic acid salt preferably at a pH of about 7 to 8. If a CysC variant polypeptide is only partially soluble in water, it may be prepared as a microemulsion by formulating it with a nonionic surfactant such as Tween, Pluronics, or PEG, e.g., Tween 80, in an amount of 0.04-0.05% (w/v), to increase its solubility.

Optionally other ingredients may be added such as antioxidants, e.g., ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; and sugar alcohols such as mannitol or sorbitol.

The CysC variant to be used for therapeutic administration is sterile. Sterility is readily accomplished by filtration through sterile filtration membranes (e.g., 0.2 micron membranes). The CysC variant ordinarily will be stored in lyophilized form or as an aqueous solution if it is highly stable to thermal and oxidative denaturation. The pH of the CysC variant preparations typically will be about from 6 to 8, although higher or lower pH values may also be appropriate in certain instances. It will be understood that use of certain of the foregoing excipients, carriers, or stabilizers will result in the formation of salts of the CysC variant.

If the CysC variant is to be used parenterally, therapeutic compositions containing the CysC variant generally are placed into a container having a sterile access port, for example, an intravenous solution bag or vial having a stopper pierceable by a hypodermic injection needle.

In some embodiments, the CysC variant polypeptide is formulated and dosed for site-specific delivery. Sustained release formulations may also be prepared, and include the formation of microcapsular particles and implantable articles. For preparing sustained-release CysC variant compositions, the CysC variant can be incorporated into a biodegradable matrix or microcapsule. A suitable material for this purpose is a polylactide, although other polymers of poly-(α-hydroxycarboxylic acids), such as poly-D-(-)-3-hydroxybutyric acid (EP 133,988A), can be used. Other biodegradable polymers include poly(lactones), poly(acetals), poly(orthoesters), or poly(orthocarbonates). The initial consideration here must be that the carrier itself, or its degradation products, is nontoxic in the target tissue and will not further aggravate the condition. This can be determined by routine screening in animal models of the target disorder or, if such models are unavailable, in normal animals. Numerous scientific publications document such animal models.

For obtaining a gel formulation, the CysC variant formulated in a liquid composition may be mixed with an effective amount of a water-soluble polysaccharide or synthetic polymer such as polyethylene glycol to form a gel of the proper viscosity to be applied topically. The polysaccharide that may be used includes, for example, cellulose derivatives such as etherified cellulose derivatives, including alkyl celluloses, hydroxyalkyl celluloses, and alkylhydroxyalkyl celluloses, for example, methylcellulose, hydroxyethyl cellulose, carboxymethyl cellulose, hydroxypropyl methylcellulose, and hydroxypropyl cellulose; starch and fractionated starch; agar; alginic acid and alginates; gum arabic; pullullan; agarose; carrageenan; dextrans; dextrins; fructans; inulin; mannans; xylans; arabinans; chitosans; glycogens; glucans; and synthetic biopolymers; as well as gums such as xanthan gum; guar gum; locust bean gum; gum arabic; tragacanth gum; and karaya gum; and derivatives and mixtures thereof. An exemplary gelling agent is one that is inert to biological systems, nontoxic, simple to prepare, and not too runny or viscous, and will not destabilize the CysC variant held within it.

In some embodiments, the polysaccharide is an etherified cellulose derivative, or one that is well defined, purified, and listed in USP, e.g., methylcellulose and the hydroxyalkyl cellulose derivatives, such as hydroxypropyl cellulose, hydroxyethyl cellulose, and hydroxypropyl methylcellulose. In some embodiments, the polysaccharide is methylcellulose.

The term "water soluble" as applied to the polysaccharides and polyethylene glycols is meant to include colloidal solutions and dispersions. In general, the solubility of the cellulose derivatives is determined by the degree of substitution of ether groups, and the stabilizing derivatives useful herein should have a sufficient quantity of such ether groups per anhydroglucose unit in the cellulose chain to render the derivatives water soluble. A degree of ether substitution of at least 0.35 ether groups per anhydroglucose unit is generally sufficient. Additionally, the cellulose derivatives may be in the form of alkali metal salts, for example, the Li, Na, K, or Cs salts.

If methylcellulose is employed in the gel, it can comprise about 2-5%, or about 3%, of the gel and the CysC variant is present in an amount of about 300-1000 mg per ml of gel.

The dosage to be employed is dependent upon the factors described above. In general, the variant cathepsin B is formulated and delivered to the target site or tissue at a dosage capable of establishing in the tissue a CysC variant level greater than about 0.1 ng/cc up to a maximum dose that is efficacious but not unduly toxic. This intra-tissue concentration should be maintained if possible by continuous infusion, sustained release, topical application, or injection at empirically determined frequencies.

In some embodiments, a variant CysC polypeptide is formulated and/or delivered in such a way as to facilitate or bypass crossing the blood-brain barrier. Molecules that cross the blood-brain barrier use two main mechanisms: free diffusion; and facilitated transport. Delivery of therapeutic agents to the CNS can be achieved by several methods.

One method relies on neurosurgical techniques. In the case of gravely ill patients such as accident victims or those suffering from various forms of dementia, surgical intervention is warranted despite its attendant risks. For instance, therapeutic agents can be delivered by direct physical introduction into the CNS, such as intraventricular or intrathecal injection of drugs. Intraventricular injection may be facilitated by an intraventricular catheter, for example, attached to a reservoir, such as an Ommaya reservoir. Methods of introduction may also be provided by rechargeable or biodegradable devices. Another approach is the disruption of the blood-brain barrier by substances which increase the permeability of the blood-brain barrier. Examples include intra-arterial infusion of poorly diffusible agents such as mannitol, pharmaceuticals which increase cerebrovascular permeability such as etoposide, or vasoactive agents such as leukotrienes. Neuwelt and Rappoport (1984) *Fed. Proc.* 43:214-219; Baba et al. (1991)

*J. Cereb. Blood Flow Metab.* 11:638-643; and Gennuso et al. (1993) *Cancer Invest.* 11:638-643.

Further, it may be desirable to administer the pharmaceutical agents locally to the area in need of treatment; this may be achieved by, for example, local infusion during surgery, by injection, by means of a catheter, or by means of an implant, said implant being of a porous, non-porous, or gelatinous material, including membranes, such as silastic membranes, or fibers.

Therapeutic compounds can also be delivered by using pharmacological techniques including chemical modification or screening for an analog which will cross the blood-brain barrier. The compound may be modified to increase the hydrophobicity of the molecule, decrease net charge or molecular weight of the molecule, or modify the molecule, so that it will resemble one normally transported across the blood-brain barrier. Levin (1980) *J. Med. Chem.* 23:682-684; Pardridge (1991) in: *Peptide Drug Delivery to the Brain*; and Kostis et al. (1994) *J. Clin. Pharmacol.* 34:989-996.

Encapsulation of the drug in a hydrophobic environment such as liposomes is also effective in delivering drugs to the CNS. For example WO 91/04014 describes a liposomal delivery system in which the drug is encapsulated within liposomes to which molecules have been added that are normally transported across the blood-brain barrier.

Another method of formulating the drug to pass through the blood-brain barrier is to encapsulate the drug in a cyclodextrin. Any suitable cyclodextrin which passes through the blood-brain barrier may be employed, including, but not limited to, β-cyclodextrin, α-cyclodextrin and derivatives thereof. See generally, U.S. Pat. Nos. 5,017,566, 5,002,935 and 4,983,586. Such compositions may also include a glycerol derivative as described by U.S. Pat. No. 5,153,179.

Delivery may also be obtained by conjugation of a therapeutic agent to a transportable agent to yield a new chimeric transportable therapeutic agent. For example, conjugation to a monoclonal antibody (Mab) to the specific carrier molecule transferrin receptor, which facilitated the uptake of the Mab conjugate through the blood-brain barrier, can be carried out. Pardridge (1991); and Bickel et al. (1993) *Proc. Natl. Acad. Sci. USA* 90:2618-2622. Several other specific transport systems have been identified, these include, but are not limited to, those for transferring insulin, or insulin-like growth factors I and II. Other suitable, non-specific carriers include, but are not limited to, pyridinium, fatty acids, inositol, cholesterol, and glucose derivatives. Certain prodrugs have been described whereby, upon entering the central nervous system, the drug is cleaved from the carrier to release the active drug. U.S. Pat. No. 5,017,566.

Other systems and methods that provide for transport of a therapeutic agent such as a protein across the BBB include use of an artificial low-density lipoprotein carrier (U.S. Pat. No. 7,220,833); conjugation of the polypeptide to an oligomer that comprises a lipophilic moiety coupled to a hydrophilic moiety (U.S. Pat. No. 6,943,148); use of a non-invasive transnasal and transocular drug delivery to the central nervous system using iontophoresis technology, e.g., as described in U.S. Pat. No. 7,200,432; etc.

Nucleic Acids Encoding Variant CysC

In some embodiments, a CysC variant is delivered to a cell by administering a nucleic acid comprising a nucleotide sequence encoding the variant CysC, where such a nucleic acid is referred to as a "variant CysC nucleic acid."

In some embodiments, the variant CysC-encoding nucleotide sequence is operably linked to a neuron-specific promoter. In other embodiments, the variant CysC-encoding nucleotide sequence is operably linked to a glial cell-specific promoter. In other embodiments, the variant CysC-encoding nucleotide sequence is operably linked to a non-neuronal cell-specific promoter. For example, in some embodiments, the variant CysC-encoding nucleotide sequence is operably linked to a ubiquitin promoter. Other suitable promoters are discussed below.

Depending on the host/vector system utilized, any of a number of suitable transcription and translation control elements, including constitutive and inducible promoters, transcription enhancer elements, transcription terminators, etc. may be used in the expression vector (see, e.g., Bitter et al. (1987) Methods in Enzymology, 153:516-544). In some embodiments, regulatory elements include regulatory elements that result in neuronal cell-specific expression of the operably linked variant CysC polypeptide-encoding nucleic acid. Neuronal cell-specific regulatory elements (including promoters, enhancers, and the like) are known to those skilled in the art. Examples of neuronal cell-specific regulatory elements include those from a neuron-specific enolase (NSE) gene (Hannas-Djebarra et al. (1997) *Brain Res. Mol. Brain Res.* 46:91-99); a PDGF gene; a Th1 gene (e.g., mouse Thy1.2 (Caroni et al. (1997) *J. Neurosci. Methods* 71:3-9); a neurofilament gene (e.g., NF-L, NF-M, and NF-L); a glial filament acidic protein gene; a myelin basic protein gene; a microtubule associated protein genes; a synaptophysin gene; a tyrosine hydroxylase gene; and the like.

In some embodiments, the variant CysC polypeptide-encoding nucleotide sequence is operably linked to an inducible promoter. Suitable inducible promoters include, but are not limited to, the pL of bacteriophage λ; Plac; Ptrp; Ptac (Ptrp-lac hybrid promoter); an isopropyl-beta-D-thiogalactopyranoside (IPTG)-inducible promoter, e.g., a lacZ promoter; a tetracycline-inducible promoter; an arabinose inducible promoter, e.g., PBAD (see, e.g., Guzman et al. (1995) J. Bacteriol. 177:4121-4130); a xylose-inducible promoter, e.g., Pxyl (see, e.g., Kim et al. (1996) Gene 181:71-76); a GAL1 promoter; a tryptophan promoter; a lac promoter; an alcohol-inducible promoter, e.g., a methanol-inducible promoter, an ethanol-inducible promoter; a raffinose-inducible promoter; a heat-inducible promoter, e.g., heat inducible lambda PL promoter, a promoter controlled by a heat-sensitive repressor (e.g., CI857-repressed lambda-based expression vectors; see, e.g., Hoffmann et al. (1999) FEMS Microbiol Lett. 177(2): 327-34); and the like.

A variant CysC nucleic acid can be administered to an individual and/or applied to a cell or tissue, where the nucleic acid is formulated with one or more pharmaceutically acceptable excipients or carriers. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

There are two major approaches to introducing the variant CysC nucleic acid (e.g., a nucleic acid contained in an expression vector) into the subject's cells for purposes of gene therapy: in vivo and ex vivo. For in vivo delivery, the nucleic acid is introduced directly into the subject. For ex vivo treatment, the subject's cells are removed, the nucleic acid is introduced into the isolated cells and the modified cells are administered to the subject either directly or, for example, encapsulated within porous membranes which are implanted into the subject. See, e.g. U.S. Pat. Nos. 4,892,538 and 5,283,187, both of which are herein expressly incorporated by reference in their entireties.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retrovirus.

Expression vectors may be used to introduce the gene into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

An example of an in vivo nucleic acid transfer technique includes transfection with viral vectors (such as adenovirus, a lentivirus vector, Herpes simplex I virus, or adeno-associated virus) and lipid-based systems (where useful lipids for lipid-mediated transfer of the gene include DOTMA, DOPE and DC-Chol, for example). In some situations it is desirable to provide the nucleic acid source with an agent that targets the target cells (e.g., a neuronal cell, a glial cell, a non-neuronal cell that produces cathepsin B, etc.), such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g., capsid proteins or fragments thereof tropic for a particular cell type, antibodies for proteins which undergo internalization in cycling, and proteins that target intracellular localization and enhance intracellular half-life. The technique of receptor-mediated endocytosis is described, for example, by Wu et al., 1987, J Biol Chem, 262:4429-4432; and Wagner et al., 1990, Proc Natl Acad Sci USA, 87: 3410-3414. For a review of the currently known gene marking and gene therapy protocols, see Anderson et al., 1992, Science, 256: 808-813 and WO 93/25673 and the references cited therein.

Small Molecule Inhibitors

In some embodiments, an active agent is a small molecule inhibitor of cystatin C. An agent that reduces CysC levels and/or activity is also referred to herein as an "active agent." In some embodiments, an active agent is a small molecule, e.g., a small organic or inorganic compound having a molecular weight of more than 50 and less than about 2,500 daltons. Agents may comprise functional groups necessary for structural interaction with proteins, particularly hydrogen bonding, and may include at least an amine, carbonyl, hydroxyl or carboxyl group, and may contain at least two of the functional chemical groups. The agents may comprise cyclical carbon or heterocyclic structures and/or aromatic or polyaromatic structures substituted with one or more of the above functional groups. Agents are also found among biomolecules including peptides, saccharides, fatty acids, steroids, purines, pyrimidines, derivatives, structural analogs or combinations thereof.

A small molecule agent (an "active agent") can be formulated in a composition with one or more pharmaceutically acceptable excipients, a variety of which are known in the art and need not be discussed in detail herein. Pharmaceutically acceptable excipients have been amply described in a variety of publications, including, for example, A. Gennaro (1995) "Remington: The Science and Practice of Pharmacy", 19th edition, Lippincott, Williams, & Wilkins.

In the subject methods, the active agent(s) may be administered to the host using any convenient means capable of resulting in the desired increase in cysteine protease activity levels. Thus, the agent can be incorporated into a variety of formulations for therapeutic administration. More particularly, an active agent can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. An active agent can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the active agent in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the unit dosage form depend on the particular active agent employed and the effect to be achieved, and the pharmacodynamics associated with each compound in the host.

Other modes of administration will also find use with the subject invention. For instance, an agent of the invention can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), e.g., about 1% to about 2%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

An active agent can be administered as injectables. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the agent adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Antibodies

In some embodiments, an agent that selectively reduces cystatin C-levels and/or activity is an antibody specific for cystatin C.

Antibodies include, but are not limited to, polyclonal, monoclonal, multispecific, human, humanized or chimeric antibodies, single chain antibodies, Fab fragments, F(ab') fragments, fragments produced by a Fab expression library, and epitope-binding fragments of any of the above. The term "antibody," as used herein, refers to molecules that contain an antigen binding site that immunospecifically binds an antigen, including Fab, Fab' and F(ab')2, Fd, single-chain Fvs (scFv), single-chain antibodies, disulfide-linked Fvs (sdFv) and fragments comprising either a $V_L$ or $V_H$ domain. The antibodies may be from human or non-human origin, e.g., murine (e.g., mouse and rat), donkey, sheep, rabbit, goat, guinea pig, camel, horse, or chicken. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

Antibodies of the present invention may also be described or specified in terms of their binding affinity to a polypeptide of the invention. Exemplary binding affinities include those with a dissociation constant or Kd less than $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, etc.

In some embodiments, an antibody specific for cystatin C is a humanized antibody. In general, humanized antibodies are made by substituting amino acids in the framework regions of a parent non-human antibody to produce a modified antibody that is less immunogenic in a human than the parent non-human antibody. Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska. et al., PNAS 91:969-973 (1994)), and chain shuffling (U.S. Pat. No. 5,565,332). In certain embodiments, framework substitutions are identified by modeling of the interactions of the CDR and framework residues to identify framework residues important for antigen binding and sequence comparison to identify unusual framework residues at particular positions (see, e.g., U.S. Pat. No. 5,585,089; Riechmann et al., Nature 332:323 (1988)). Additional methods for humanizing antibodies contemplated for use in the present invention are described in U.S. Pat. Nos. 5,750,078; 5,502,167; 5,705,154; 5,770,403; 5,698,417; 5,693,493; 5,558,864; 4,935,496; and 4,816,567, and PCT publications WO 98/45331 and WO 98/45332. In particular embodiments, a suitable anti-CysC antibody may be humanized according to the methods set forth in published U.S. patent applications 20040086979 and 20050033031. Accordingly, a suitable anti-CysC antibody can be humanized using methods that are well known in the art.

The invention also provides antibodies that competitively inhibit binding of a CysC polypeptide to a CatB polypeptide as determined by any method known in the art for determining competitive binding, for example, the immunoassays described herein. In some embodiments, the antibody competitively inhibits binding of a CysC polypeptide to a CatB polypeptide by at least 95%, at least 90%, at least 85%, at least 80%, at least 75%, at least 70%, at least 60%, or at least 50%. Antibody production methods are well known in the art.

An anti-CysC antibody can be formulated in a composition with one or more pharmaceutically acceptable excipients, a variety of which are known in the art and need not be discussed in detail herein. Pharmaceutically acceptable excipients have been amply described in a variety of publications, including, for example, A. Gennaro (1995) "Remington: The Science and Practice of Pharmacy", 19th edition, Lippincott, Williams, & Wilkins.

In the subject methods, the anti-CysC antibody may be administered to the host using any convenient means capable of resulting in the desired increase in cathepsin B activity levels. Thus, the anti-CysC antibody can be incorporated into a variety of formulations for therapeutic administration. More particularly, an anti-CysC antibody can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, the anti-CysC antibody may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the anti-CysC antibody can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The anti-CysC antibody can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The anti-CysC antibody can be utilized in aerosol formulation to be administered via inhalation. An anti-CysC antibody can be formulated into pressurized acceptable propellants such as dichlorodifluoromethane, propane, nitrogen and the like.

The term "unit dosage form," as used herein, refers to physically discrete units suitable as unitary dosages for human and animal subjects, each unit containing a predetermined quantity of anti-CysC antibody calculated in an amount sufficient to produce the desired effect in association with a pharmaceutically acceptable diluent, carrier or vehicle.

Other modes of administration will also find use with the subject invention. For instance, an anti-CysC antibody can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), e.g., about 1% to about 2%.

An anti-CysC antibody can be administered as injectables. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the anti-CysC antibody adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Peptide Agents

In some embodiments, an agent that selectively reduces cystatin C levels and/or activity is a peptide agent.

In some embodiments, a peptide agent is a fragment of cystatin C that inhibits binding of cystatin C to cathepsin B. In some embodiments, a peptide agent has a length of from about 5 amino acids to about 50 amino acids, e.g., from about 5 amino acids to about 10 amino acids, from about 10 amino acids to about 15 amino acids, from about 15 amino acids to about 20 amino acids, from about 20 amino acids to about 25 amino acids, from about 25 amino acids to about 30 amino acids, from about 30 amino acids to about 40 amino acids, or from about 40 amino acids to about 50 amino acids.

In some embodiments, a peptide agent comprises from about 5 amino acids to about 50 amino acids of any one of the following amino acid sequences:

1) $NH_2$-nkasndmyhs ralqvvrark qivagvnyfl dvelgrttct ktqpnldncp-COOH (SEQ ID NO:3), corresponding to amino acids 61-110 of the amino acid sequence depicted in FIG. 8A;

2) nkgsndayhs raiqvvrark qlvagvnyfl dvemgrttct ksqtnitdcp (SEQ ID NO:4);

3) nkgsndayhs raiqvvrark qlvaginyyl dvemgrttct ksqtnitncp (SEQ ID NO:5);

4) nkgsndryhs ralqvvrarr qivsgvkyyl dvligrttct ktqtnlancp (SEQ ID NO:6).

or an active variant of one of SEQ ID NOs3-6.

Peptides can include naturally-occurring and non-naturally occurring amino acids. Peptides may comprise D-amino acids, a combination of D- and L-amino acids, and various "designer" amino acids (e.g., β-methyl amino acids, Cα-methyl amino acids, and Nα-methyl amino acids, etc.) to convey special properties to peptides. Additionally, peptide may be a cyclic peptide. Peptides may include non-classical amino acids in order to introduce particular conformational motifs. Any known non-classical amino acid can be used. Non-classical amino acids include, but are not limited to, 1,2,3,4-tetrahydroisoquinoline-3-carboxylate; (2S,3S)-methylphenylalanine, (2S,3R)-methyl-phenylalanine, (2R,3S)-methyl-phenylalanine and (2R,3R)-methyl-phenylalanine; 2-aminotetrahydronaphthalene-2-carboxylic acid; hydroxy-1,2,3,4-tetrahydroisoquinoline-3-carboxylate; β-carboline (D and L); HIC (histidine isoquinoline carboxylic acid); and HIC (histidine cyclic urea). Amino acid analogs and peptidomimetics may be incorporated into a peptide to induce or favor specific secondary structures, including, but not limited to, LL-Acp (LL-3-amino-2-propenidone-6-carboxylic acid), a β-turn inducing dipeptide analog; β-sheet inducing analogs; β-turn inducing analogs; α-helix inducing analogs; γ-turn inducing analogs; Gly-Ala turn analog; amide bond isostere; tretrazol; and the like.

A peptide may be a depsipeptide, which may be a linear or a cyclic depsipeptide. Kuisle et al. (1999) *Tet. Letters* 40:1203-1206. "Depsipeptides" are compounds containing a sequence of at least two alpha-amino acids and at least one alpha-hydroxy carboxylic acid, which are bound through at least one normal peptide link and ester links, derived from the hydroxy carboxylic acids, where "linear depsipeptides" may comprise rings formed through S—S bridges, or through an hydroxy or a mercapto group of an hydroxy-, or mercapto-amino acid and the carboxyl group of another amino- or hydroxy-acid but do not comprise rings formed only through peptide or ester links derived from hydroxy carboxylic acids.

"Cyclic depsipeptides" are peptides containing at least one ring formed only through peptide or ester links, derived from hydroxy carboxylic acids.

Peptides may be cyclic or bicyclic. For example, the C-terminal carboxyl group or a C-terminal ester can be induced to cyclize by internal displacement of the —OH or the ester (—OR) of the carboxyl group or ester respectively with the N-terminal amino group to form a cyclic peptide. For example, after synthesis and cleavage to give the peptide acid, the free acid is converted to an activated ester by an appropriate carboxyl group activator such as dicyclohexylcarbodiimide (DCC) in solution, for example, in methylene chloride ($CH_2Cl_2$), dimethyl formamide (DMF) mixtures. The cyclic peptide is then formed by internal displacement of the activated ester with the N-terminal amine. Internal cyclization as opposed to polymerization can be enhanced by use of very dilute solutions. Methods for making cyclic peptides are well known in the art The term "bicyclic" refers to a peptide in which there exists two ring closures. The ring closures are formed by covalent linkages between amino acids in the peptide. A covalent linkage between two nonadjacent amino acids constitutes a ring closure, as does a second covalent linkage between a pair of adjacent amino acids which are already linked by a covalent peptide linkage. The covalent linkages forming the ring closures may be amide linkages, i.e., the linkage formed between a free amino on one amino acid and a free carboxyl of a second amino acid, or linkages formed between the side chains or "R" groups of amino acids in the peptides. Thus, bicyclic peptides may be "true" bicyclic peptides, i.e., peptides cyclized by the formation of a peptide bond between the N-terminus and the C-terminus of the peptide, or they may be "depsi-bicyclic" peptides, i.e., peptides in which the terminal amino acids are covalently linked through their side chain moieties.

A desamino or descarboxy residue can be incorporated at the terminii of the peptide, so that there is no terminal amino or carboxyl group, to decrease susceptibility to proteases or to restrict the conformation of the peptide. C-terminal functional groups include amide, amide lower alkyl, amide di(lower alkyl), lower alkoxy, hydroxy, and carboxy, and the lower ester derivatives thereof, and the pharmaceutically acceptable salts thereof.

In addition to the foregoing N-terminal and C-terminal modifications, a peptide or peptidomimetic can be modified with or covalently coupled to one or more of a variety of hydrophilic polymers to increase solubility and circulation half-life of the peptide. Suitable nonproteinaceous hydrophilic polymers for coupling to a peptide include, but are not limited to, polyalkylethers as exemplified by polyethylene glycol and polypropylene glycol, polylactic acid, polyglycolic acid, polyoxyalkenes, polyvinylalcohol, polyvinylpyrrolidone, cellulose and cellulose derivatives, dextran and dextran derivatives, etc. Generally, such hydrophilic polymers have an average molecular weight ranging from about 500 to about 100,000 daltons, from about 2,000 to about 40,000 daltons, or from about 5,000 to about 20,000 daltons. The peptide can be derivatized with or coupled to such polymers using any of the methods set forth in Zallipsky, S., Bioconjugate Chem., 6:150-165 (1995); Monfardini, C, et al., Bioconjugate Chem., 6:62-69 (1995); U.S. Pat. Nos. 4,640,835; 4,496,689; 4,301,144; 4,670,417; 4,791,192; 4,179,337 or WO 95/34326.

Another suitable agent for reducing an activity of a subject sulfatase is a peptide aptamer. Peptide aptamers are peptides or small polypeptides that act as dominant inhibitors of protein function. Peptide aptamers specifically bind to target proteins, blocking their function ability. Kolonin and Finley, PNAS (1998) 95:14266-14271. Due to the highly selective nature of peptide aptamers, they may be used not only to target a specific protein, but also to target specific functions of a given protein (e.g. a signaling function). Further, peptide aptamers may be expressed in a controlled fashion by use of promoters which regulate expression in a temporal, spatial or inducible manner. Peptide aptamers act dominantly; therefore, they can be used to analyze proteins for which loss-of-function mutants are not available.

Peptide aptamers that bind with high affinity and specificity to a target protein may be isolated by a variety of techniques known in the art. Peptide aptamers can be isolated from random peptide libraries by yeast two-hybrid screens (Xu et al., PNAS (1997) 94:12473-12478). They can also be isolated from phage libraries (Hoogenboom et al., Immunotechnology (1998) 4:1-20) or chemically generated peptides/libraries.

Subjects Suitable for Treatment

A subject treatment method is suitable for treating an individual in need thereof, e.g., an individual who has been diagnosed as having Alzheimer's disease. In some embodiments, an individual in need of treatment with a subject method is an individual having a cerebral angiopathy. In other embodiments, an individual in need of treatment with a subject method has suffered microhemorrhage as a result of immunotherapy.

Whether a subject method for treating AD is effective can be determined using any known method, e.g., measuring cognitive function, learning, memory, and the like.

Screening Methods

The present invention provides methods for identifying an agent that reduces cystatin C levels and/or activity. The present invention provides methods for identifying an agent that selectively reduces cystatin-C-mediated inhibition of cathepsin B enzymatic activity. The methods generally involve: a) forming a test sample by contacting a test agent with a mixture comprising: i) a substrate for cathepsin B; ii) a cystatin C polypeptide; and iii) a cathepsin B polypeptide; and b) determining (e.g., testing) the effect, if any, of the test agent on the level of cathepsin B activity in the test sample, compared to the level of cathepsin B activity in a control sample lacking the test agent. A test agent that reduces cystatin C levels and/or activity results in an increased level of cathepsin B activity compared to the level of cathepsin B activity in the control sample. A suitable control sample includes: i) cathepsin B; ii) substrate for cathepsin B; iii) cystatin C; and does not include the test agent. The effect of the test agent on the level and/or activity of cystatin C in the test sample is readily assessed by testing cathepsin B activity level in the test sample, and in the control sample.

A test agent of interest is a test agent that increases the level cathepsin B activity by at least about 10%, at least about 20%, at least about 30%, at least about 40%, at least about 50%, at least about 60%, at least about 70%, at least about 80%, at least about 90%, at least about 2-fold, at least about 5-fold, at least about 10-fold, or at least about 20-fold, or more, compared to (relative to) the level of cathepsin B activity in the control sample. A test agent of interest is one that reduces cystatin C levels and/or activity; and thus reduces amyloid beta levels in a cell or tissue. A test agent of interest is thus a candidate agent for the treatment of AD, for the treatment of a cerebral angiopathy, etc.

The terms "candidate agent," "test agent," "agent," "substance," and "compound" are used interchangeably herein. Candidate agents encompass numerous chemical classes, typically synthetic, semi-synthetic, or naturally-occurring inorganic or organic molecules.

Candidate agents include those found in large libraries of synthetic or natural compounds. For example, synthetic compound libraries are commercially available from Maybridge Chemical Co. (Trevillet, Cornwall, UK), ComGenex (South San Francisco, Calif.), and MicroSource (New Milford, Conn.). A rare chemical library is available from Aldrich (Milwaukee, Wis.). Alternatively, libraries of natural compounds in the form of bacterial, fungal, plant and animal extracts are available from Pan Labs (Bothell, Wash.) or are readily producible.

Candidate agents may be small organic or inorganic compounds having a molecular weight of more than 50 and less than about 2,500 daltons. Candidate agents may comprise functional groups necessary for structural interaction with other macromolecules such as proteins, e.g., hydrogen bonding, and may include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Assays of the invention include controls, where suitable controls include a sample in the absence of the test agent. Generally a plurality of assay mixtures is run in parallel with different test agent concentrations to obtain a differential response to the various concentrations. Typically, one of these concentrations serves as a negative control, i.e. at zero concentration or below the level of detection.

Cathepsin B activity can be measured using any available method. For example, cathepsin B levels can be detected using the Innozyme Cathepsin B Activity Assay Kit (EMD Biosciences). For example, a fluorogenic peptide substrate is used which provides for a fluorescent signal upon action on the substrate by cathepsin B. Fluorogenic peptide substrates of cathepsin B are known. See, e.g., Stachowiak et al. (2004) *Acta Biochimica Polonica* 51:81-92; and Barrett (1980) *Biochem. J.* 187:909. Non-limiting examples of fluorogenic substrates for cathepsin B include: Benzyloxycarbonyl-phenylalanyl-arginine 4-methyl-7-coumarylamide; and N-benzyloxycarbonyl-L-arginyl-L-arginine 2-naphthylamide.

Amino acid sequences of various cathepsin B polypeptides are known, and any known cathepsin B can be used. See, e.g., Chan et al. (1986) *Proc. Natl. Acad. Sci. USA* 83:7721-7725, for human and mouse preprocathepsin B polypeptides. See also GenBank Accession No. AAH10240 (*Homo sapiens* procathepsin B). Nucleotide sequences encoding cathepsin B are also known. See, e.g., GenBank Accession No. BC01240. Preprocathepsin B polypeptide has a length of about 339 amino acids; mature cathepsin B (amino acids 81-328 of the preprocathepsin B) is about 248 amino acids in length. In some embodiments, the cathepsin B polypeptide that is used is the mature form.

In some embodiments, the cathepsin B polypeptide has a length of from about 200 amino acids to about 225 amino acids, from about 225 amino acids to about 250 amino acids (e.g., about 248 amino acids), from about 250 amino acids to about 275 amino acids, from about amino acids to about 275 amino acids, from about 300 amino acids, or from about 300 amino acids to about 339 amino acids.

In some embodiments, a suitable cathepsin B polypeptide comprises an amino acid sequence having at least about 75%, at least about 80%, at least about 85%, at least about 90%, at least about 95%, at least about 98%, at least about 99%, or more, amino acid sequence identity with the amino acid sequence set forth in SEQ ID NO:11. In some embodiments, a suitable cathepsin B polypeptide comprises an amino acid sequence having at least about 75%, at least about 80%, at least about 85%, at least about 90%, at least about 95%, at least about 98%, at least about 99%, or more, amino acid sequence identity with amino acids 81-328 of the amino acid sequence set forth in SEQ ID NO:11.

In some embodiments, a suitable cystatin C polypeptide comprises an amino acid sequence having at least about 75%, at least about 80%, at least about 85%, at least about 90%, at least about 95%, at least about 98%, at least about 99%, or more, amino acid sequence identity with the amino acid sequence set forth in SEQ ID NO:1.

Pathological Studies

A test agent of interest can be further evaluated for efficacy of reducing Aβ levels in an animal model, e.g., an animal model of AD. After exposure to the candidate agent, the animals are sacrificed and analyzed by immunohistology for, e.g.: 1) levels of neurofibrillary tangles (NFTs) in the brain and/or 2) levels of Aβ in the brain and/or 3) neuronal loss and/or 4) other neuropathologies. The brain tissue is fixed (e.g, in 4% paraformaldehyde) and sectioned; the sections are stained with antibodies reactive with Aβ, and/or p-tau, and/or p-NF—H. Secondary antibodies conjugated with fluorescein, rhodamine, horse radish peroxidase, or alkaline phosphatase are used to detect the primary antibody. These experiments permit identification of neurofibrillary tangles and Aβ deposition and the regionalization of these NFTs to specific areas of the brain.

Sections can also be stained with other diagnostic antibodies recognizing antigens such as A1z-50, A2B5, neuron-specific enolase, and others that are characteristic of neurodegeneration. Staining with thioflavins and congo red can also be carried out to analyze co-localization of Aβ deposits within the neuritic plaques and NFTs.

Behavioral Studies

A candidate agent can be further evaluated for its effect on behavioral parameters, e.g., learning and memory. Behavioral tests designed to assess learning and memory deficits can be employed. An example of such as test is the Morris Water maze (Morris *Learn Motivat* 12:239-260 (1981)). In this procedure, the animal is placed in a circular pool filled with water, with an escape platform submerged just below the surface of the water. A visible marker is placed on the platform so that the animal can find it by navigating toward a proximal visual cue. Alternatively, a more complex form of the test in which there are no formal cues to mark the platform's location will be given to the animals. In this form, the animal must learn the platform's location relative to distal visual cues. Alternatively, or in addition, memory and learning deficits can be studied using a 3 runway panel for working memory impairment (attempts to pass through two incorrect panels of the three panel-gates at four choice points) (Ohno et al. *Pharmacol Biochem Behav* 57:257-261 (1997)).

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Regulation of CatB Activity by CysC

CysC, the endogenous inhibitor of CatB, is present in a subpopulation of senile plaques.

It has been found that CatB levels are higher in both young (1-3 months) and middle-aged (6-8 months) hAPP transgenic mice than in age-matched non-transgenic controls, but not in old (16-20 month-old) hAPP mice (FIG. 1A). CysC expression was analyzed in 6-7 month-old (FIGS. 1B) and 16-20 month-old (FIG. 1C) hAPP mice. In middle-aged hAPP mice, which have higher CatB activity than non-transgenic (Ntg) controls, CysC levels were significantly reduced. However, CysC levels appeared higher in old hAPP mice, consistent with the notion that higher levels of CysC counteract CatB activities during aging.

Figure 1B:
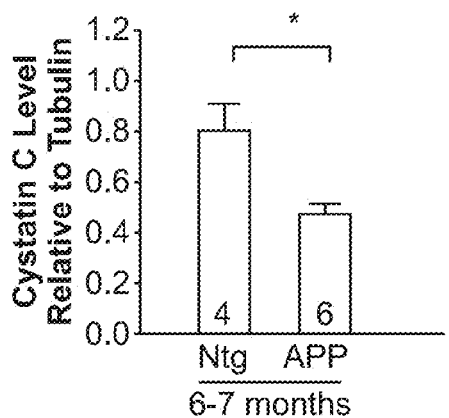
Figure 1C:
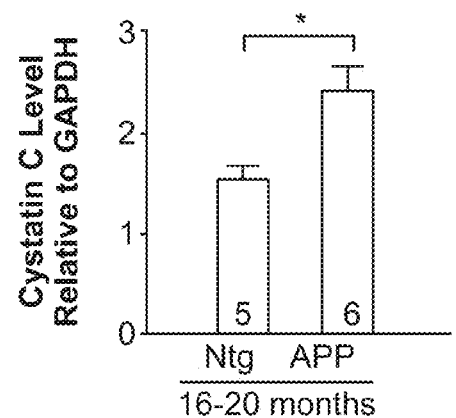

FIGS. 1A and 1B. CatB activity and CysC levels in hAPP mice. The number of animals/group is indicated inside the bars. Bars represent means±SEM. (A) Hippocampal CatB activities were measured in hAPP mice and their age-matched Ntg controls at 1-3, 7-8, and 16-20 months of age. (*, P<0.05; **, P<0.01; Tukey-Kramer post hoc test). (B-C) Western blots were used to quantify relative CysC levels in 6-8 (B) and 16-20 month-old hAPP mice (C) and their non-transgenic (Ntg) controls (*, P<0.05, Student t test).

Genetic Ablation of CysC Increases CatB Activity.

CysC-null (CysC$^{-/-}$) mice were crossed with C57B1/6 wild-type mice to generate CysC$^{+/-}$ mice, which were crossed again to generate CysC$^{-/-}$ and littermate CysC$^{+/+}$ wild-type controls. Hippocampal CatB activities, measured with the Innozyme Cathepsin B Activity Assay Kit (EMD Biosciences), were significantly higher in CysC$^{-/-}$ mice than in wild-type CysC$^{+/+}$ controls (FIG. 2A), supporting the notion that CysC is the main endogenous inhibitor of CatB.

Genetic Ablation of CysC Reduces $A\beta_{1-42}$ Levels in Primary Cortical Neurons.

Cortical neurons were isolated from mouse pups of a cross between CysC$^{+/-}$ mice on postnatal day 0 or 1 and individually cultured. CysC$^{-/-}$ or CysC$^{+/+}$ cultures were infected with an adenoviral vector encoding hAPP cDNA under the cytomegalovirus (CMV) promoter (MOI=10-20) on day 4. Three days later, the supernatants were harvested for Aβ ELISA. Cells were harvested for CatB activity assay, and BCA (Pierce) protein assays. Levels of $A\beta_{1-42}$ (FIG. 2B), but not total $A\beta_{1-x}$ (FIG. 2C), were significantly lower in the supernatants from CysC$^{-/-}$ cultures than CysC$^{+/+}$ cultures, suggesting that removal of CysC, which promotes CatB activity, reduces $A\beta_{1-42}$ levels. Removal of CatB resulted in higher $A\beta_{1-42}$ levels (FIG. 2B).

FIGS. 2A-C. (A) CatB activity in hippocampal lysates is significantly higher in CysC$^{-/-}$ mice (n=6) than in wild-type CysC$^{+/+}$ mice (n=6; * P<0.001). Levels of $A\beta_{1-42}$ (B), but not $A\beta_{1-x}$ (C), were significantly lower than in CysC$^{-/-}$ CatB$^{+/+}$ neurons (n=6) than in wild-type CysC$^{+/+}$ CatB$^{+/+}$ neurons (n=6).  P<0.01, unpaired t test. Levels of $A\beta_{1-42}$ (B), but not $A\beta_{1-x}$ (C), were significantly higher in CatB$^{-/-}$ neurons (n=6) than in wild-type neurons (n=8) infected with hAPP adenovirus. *P<0.05, Mann-Whitney U test. Average Aβ levels in wild-type cultures were arbitrarily set as 1.

Figure 9:
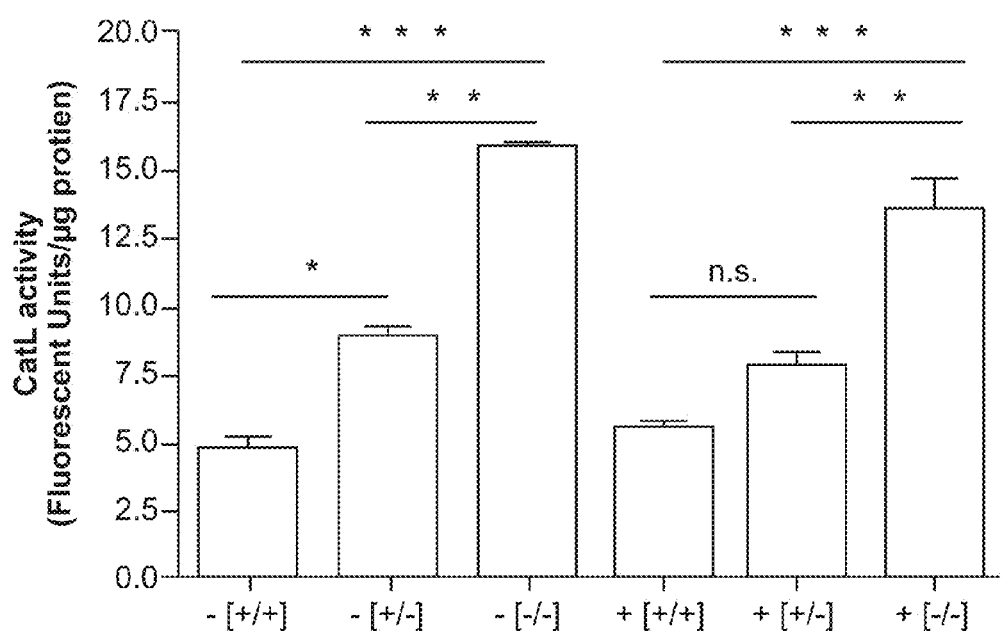
FIG. 9 depicts the effect of ablation of cysC on cathepsin L activity.

FIG. 9. Cathepsin L activity in hippocampal lysates is significantly higher in CysC$^{-/-}$ mice (n=6) than in wild-type CysC$^{+/+}$ mice (n=6; *** P<0.001).

Figure 10:
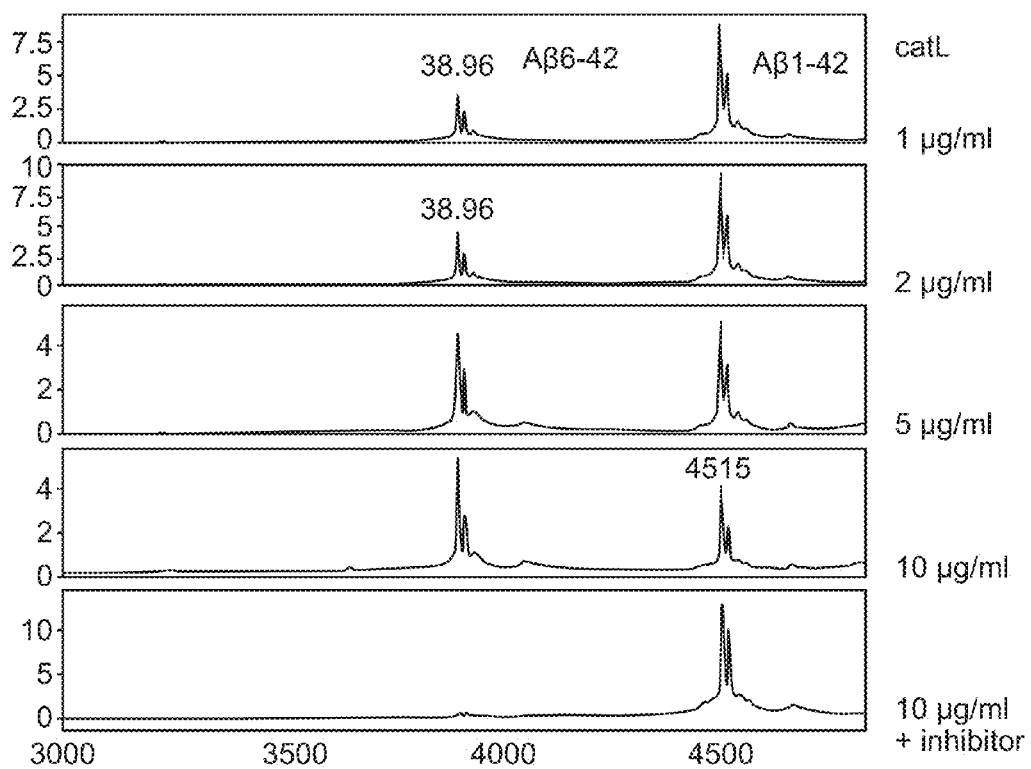
FIG. 10 depicts cleavage of $A\beta_{1-42}$ by cathepsin L.

FIG. 10. Cathepsin L cleaves Abeta1-42 at the N-terminus. The proteolytic products were analyzed with SELDI-TOF mass spectrometry. Incubating Aβ1-42 with CatL resulted in the dose-dependent generation of Aβ6-42 through proteolytic cleavage. No truncations occurred in the presence of the inhibitor, confirming that the truncations were dependent on the proteolytic activity of CatL.

Genetic Ablation of CysC Reduces Aβ Levels In vivo.

A cohort of 7-8 month old hAPP/CysC$^{-/-}$, hAPP/CysC$^{+/+}$, CysC$^{-/-}$, and CysC$^{+/+}$ mice was analyzed. The amount of plaque deposition in hAPP/CysC$^{-/-}$ mice (n=7) was markedly less than in hAPP/CysC$^{+/+}$ mice (n=9) (FIGS. 3A and 3B). Furthermore, ELISA analyses revealed that ablation of CysC significantly reduced levels of both total Aβ($A\beta_{1-x}$) and $A\beta_{1-42}$ (FIGS. 3C and 3D).

FIGS. 3A-D. Effects of CysC on plaque loads and Aβ levels in hAPP mice. (A-B). Genetic ablation of CysC decreased plaque load in hippocampus. Photomicrographs of 3D6 immunostaining in the hippocampus of 7-8-month-old hAPP/CysC$^{+/+}$ and hAPP/CysC$^{-/-}$ mice (A). Amounts of Aβ deposits were determined as the percent area of hippocampus covered by 3D6-immunoreactive material (B; n=7-9 mice/genotype; **, P<0.01, unpaired t test). (C-D) Ablating CysC decreased levels of $A\beta_{1-42}$ (C) and $A\beta_{1-x}$ (D) measured by ELISA (n=7-9 mice/genotype; *, P<0.05, unpaired t test). Bars represent means±SEM (B-D).

Figure 4A:
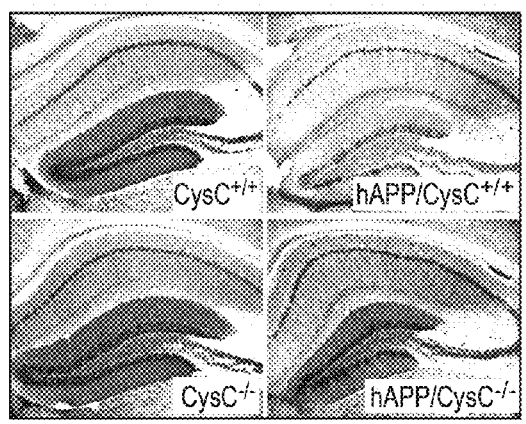
FIGS. 4A and 4B depict the effects of CysC on neuronal deficits in hAPP mice.
Figure 4B:
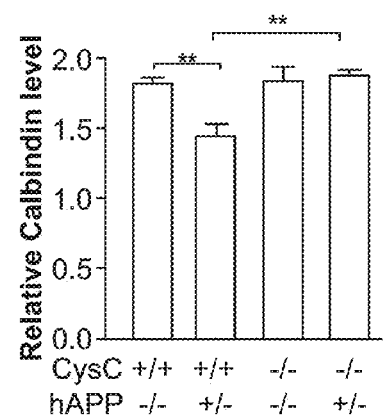

Deletion of CysC also markedly reduced the extent of neuronal deficits, measured by calbindin depletion in the dentate gyrus (FIGS. 4A and 4B).

FIGS. 4A and 4B. Effects of CysC on neuronal deficits in hAPP mice. (A) Photomicrographs of calbindin immunostaining in the hippocampus of 7-8-month-old hAPP/CysC$^{+/+}$ mice, hAPP/CysC$^{-/-}$ mice, and littermate controls that do not express human hAPP (CysC$^{+/+}$ and CysC$^{-/-}$). (B) Calbindin levels in the dentate gyrus relative to those in the CA1 regions were significantly higher in hAPP/CysC$^{-/-}$ mice than in hAPP/CysC$^{+/+}$ mice (n=7-12/genotype; **, P<0.01, Tukey Kramer post hoc test). Bars represent means±SEM (B).

Figure 11:
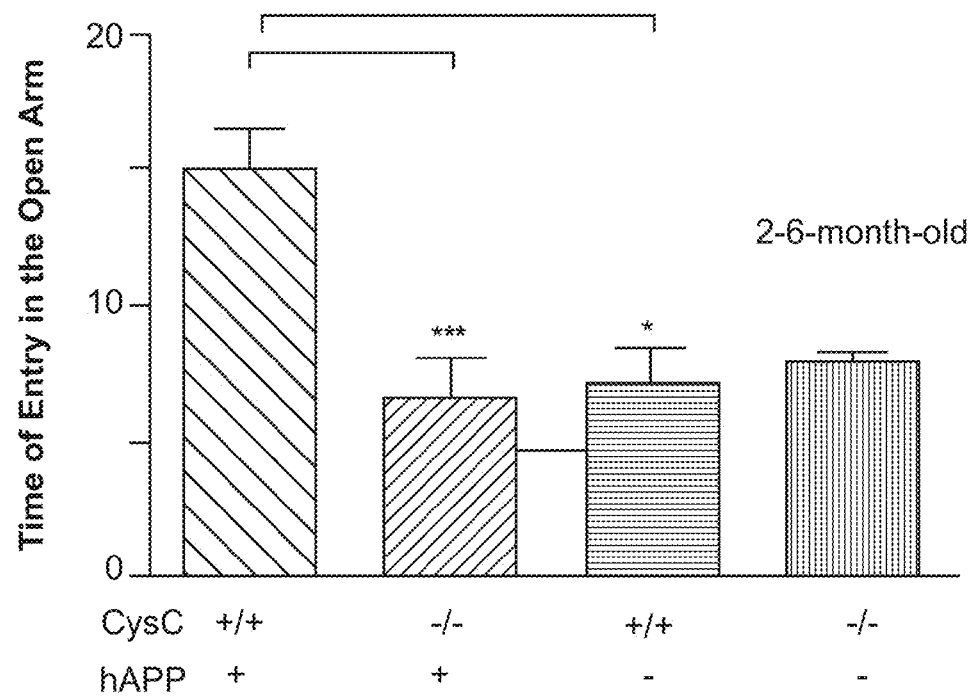
FIG. 11 depicts the effects of CysC on behavioral alterations in hAPP mice.

FIG. 11. Effects of CysC on behavioral alteration in hAPP mice. The mice were tested in the elevated plus maze, in which the percentage of time spent in the open arm reflects emotionality and exploratory behavior. The amount of time spent and distance moved in the open and closed arm, as well as the number of times the mice extended their head over the edges of the open arms, will be measured as exploratory behaviors that are also associated with anxiety. It was found that the number of times hAPP entered the open arm is significantly higher than wildtype mice. Ablation of CysC abolished this abnormality in the elevated plus maze. *, P<0.001, , P<0.01, Tukey Kramer post hoc test).

Generation of CysC Mutants that Lacks Inhibitory Function

Extensive structure and function studies revealed that the region from amino acid 64 to amino acid 94 (numbering refers to the nucleic acid at the N-terminus) was required for protease inhibitory function of CysC. Abrahamson et al. ((1987) *J. Biol. Chem.* 262:9688-9694); Abrahamson et al. ((1990) *Biochem. J.* 268:287-294); Hall et al. ((1998) *Biochem.* 37:4071-4079); and Janowski et al. ((2004) *J. Mol.*

Biol. 341:151-160). Deletion of this region (CysCΔ64-94) reduced inhibition of cathepsin B cysteine protease activity without affecting the normal trafficking and other biological functions of CysC. Lentiviral vectors expression wild-type CysC or a mutant CysC lacking the protease inhibitory domain were generated. Lenti-CysC was generated by replacing CatB cDNA in Lenti-CatB with full-length CysC (ATCC 63,113). To generate Lenti-CysCΔ64-94, we used a sequential polymerase chain reaction (PCR)-based strategy modified from Taupin et al. ((2000) *Neuron* 28:385-397).

Figure 5:
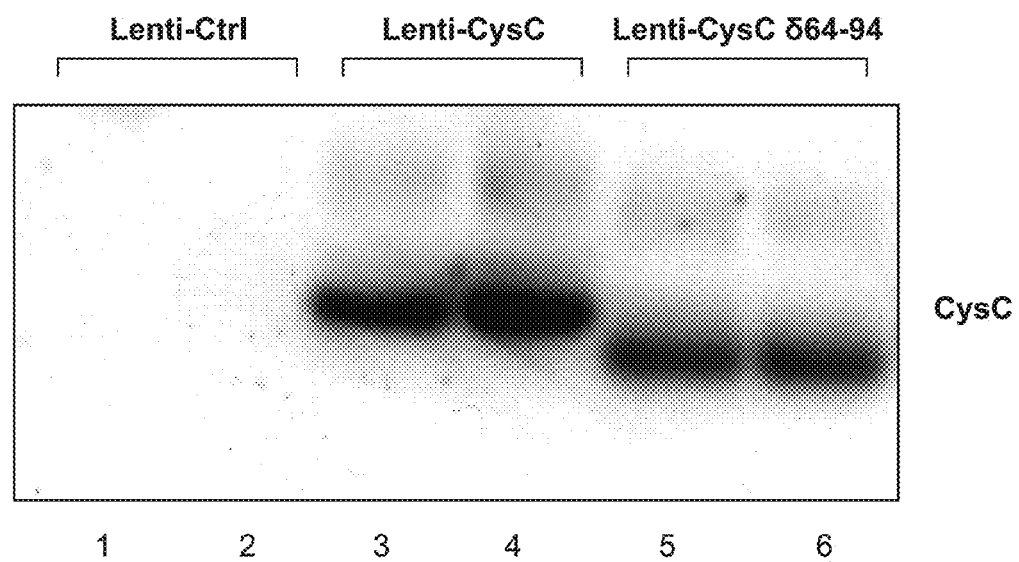
FIG. 5 depicts a Western blot of supernatants from CysC$^{-/-}$ cultures infected with control lentivirus (Lenti-ctrl), lentivirus overexpressing CysC (Lenti-CysC) and lentivirus overexpressing CysC lacking the protease inhibitory domain (Lenti-Cysδ64-94).

FIG. 5. Western blot of supernatants from CysC$^{-/-}$ cultures infected with control lentivirus (Lenti-Ctrl) (lanes 1 and 2), lentivirus overexpressing CysC (lanes 3 and 4), or lentivirus overexpressing CysC lacking protease inhibitory domain (Lenti-CysCΔ64-94) (lanes 5 and 6).

RNAi-Mediated Gene Silencing

Figure 6A:
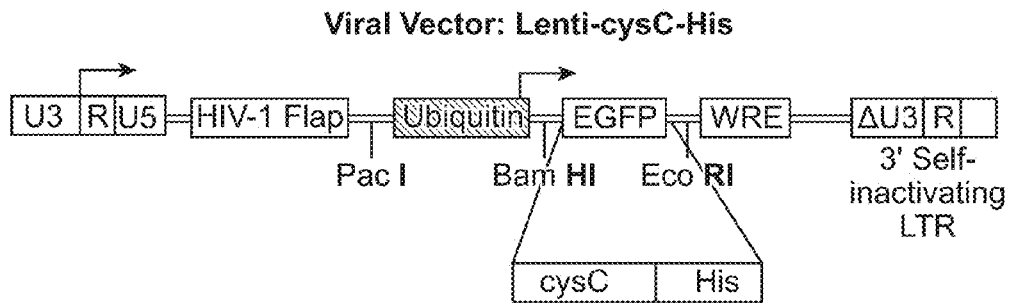
FIGS. 6A-D depict mixed cortical cultures and overexpression and knockdown of CysS mediated by lentiviral vectors.
Figure 6B:
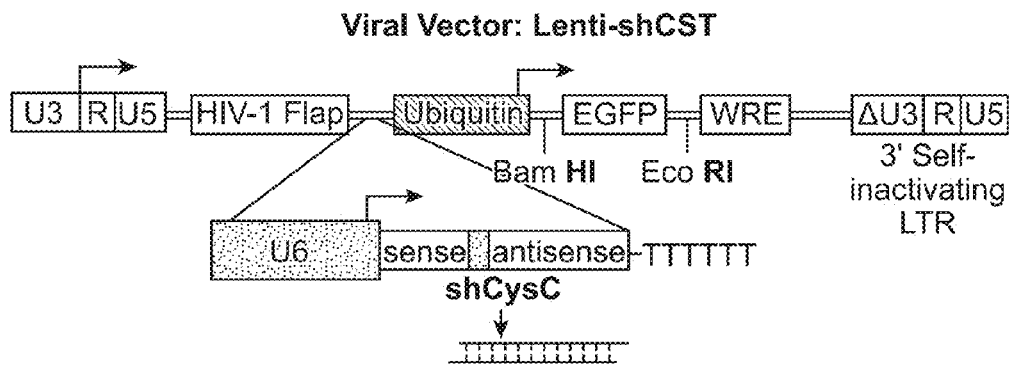
Figure 6C:
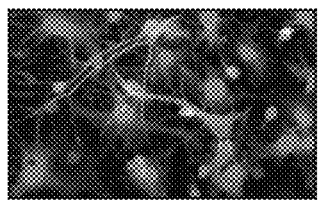
Figure 6D:
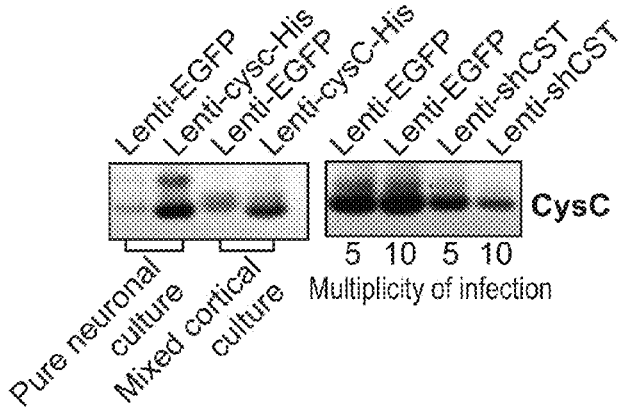

RNAi-mediated gene silencing was used to inhibit endogenous CysC expression. RNAi is an efficient method to induce gene-specific silencing in mammalian cells either by transfection of short interfering RNAs (siRNAs) or by transcription of short hairpin RNAs (shRNAs) from expression vectors, including lentiviral vectors. A recombinant lentiviral vector was constructed, which overexpressed small hairpin RNA specific for the mouse CST gene (FIG. 6C). Briefly, a double-stranded palindrome sequence corresponding to mouse CST3 (5'-gtcccagacaaatttgactttcaa-gagaagtcaaatttgtctgggacttttt-3'; SEQ ID NO:7) was cloned downstream of the U6 promoter and ligated into the lentiviral transfer vector to create Lenti-sh-CST, which also expressed EGFP (enhanced green fluorescent protein) under transcriptional control of the ubiquitin-C promoter (FIG. 6C). The ubiquitin promoter was chosen because of its ubiquitous expression pattern similar to that of U6, providing a convenient visual marker for cells expressing sh-CST. Compared with control vector (Lenti-EGFP), which expresses EGFP alone, lentivirus expressing sh-CST significantly suppressed the endogenous CysC expression in microglial BV2 cells, resulting in decrease of CysC levels in a dose-dependent manner (FIG. 6D).

FIGS. 6A-D. Mixed cortical cultures and overexpression and knockdown of CysC mediated by lentiviral vectors. A) Diagram of lentiviral vector expressing EGFP (Lenti-EGFP) or His-tagged CysC (Lenti-CysC-His). Lentiviral vector expressing EGFP and U6-driven small hairpin RNA corresponding to mouse CST3 (sh-CST) is shown in (B). Only the relevant portions of the plasmid are shown. The diagram is not drawn to proportion. (C) Expression of EGFP (green) is detected in both neurons (MAP2 staining; red) and astroglia in mixed cultures infected with Lenti-EGFP (MOI=10). (D) Overexpression of CysC is detected in the supernatant of both pure neuronal cultures and mixed cultures infected with Lenti-CysC-His using western blots with anti-CysC antibody, and downregulation of CysC is detected in the supernatant of microglial BV2 cells infected with Lenti-shCST.

Antibody Inhibition

Figure 7:
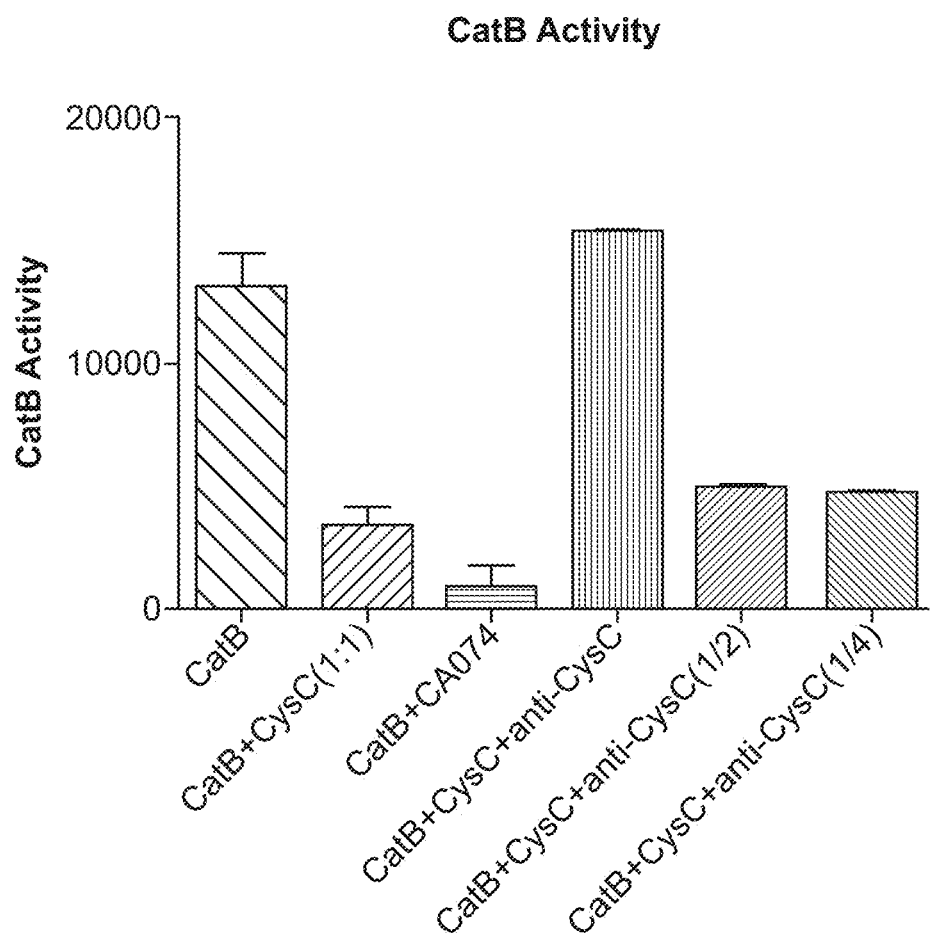
FIG. 7 depicts neutralization of CysC-mediated inhibition of CatB activity by an anti-CysC antibody.

Cathepsin B (CatB) was incubated alone, with CysC, with a cathepsin B inhibitor (CA074), or with CysC and antibody specific for CysC. The results are shown in FIG. 7. Antibody to CysC neutralizes inhibition of cathepsin D cysteine protease activity by CysC.

Figure 12:
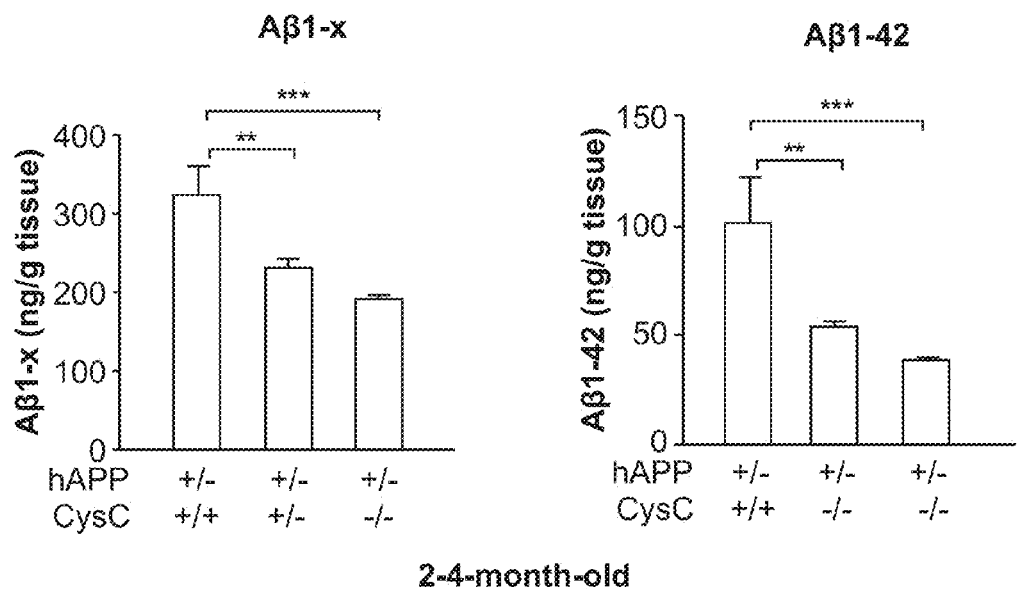
FIG. 12 depicts the effect of CysC reduction on Aβ1-x and Aβ1-42 in young hAPP mice.
Figure 13:
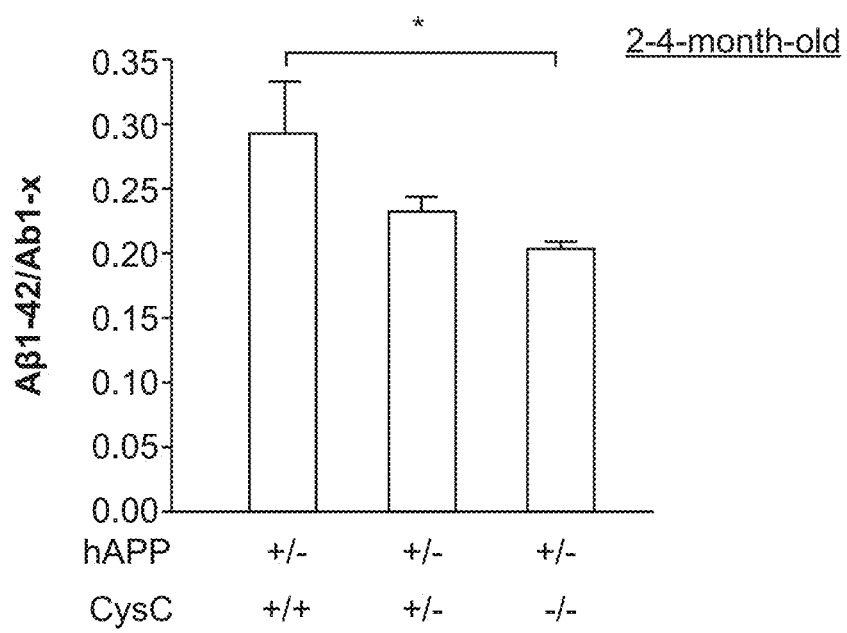
FIG. 13 depicts the effect of CysC ablation on the relative abundance of Aβ1-42 in young hAPP mice.
Figure 14:
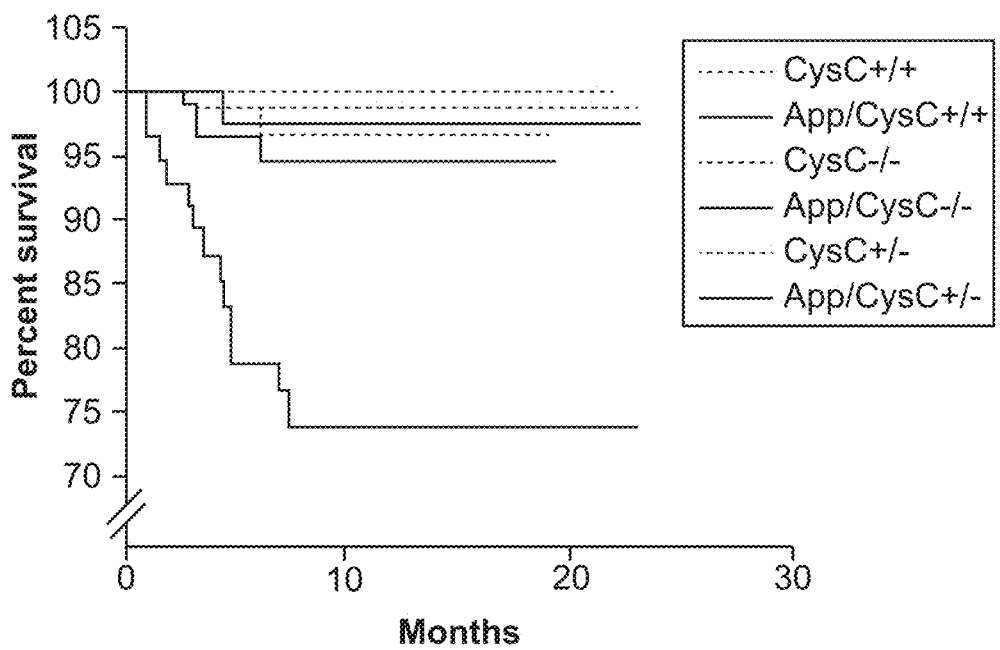
FIG. 14 depicts the effect of CysC reduction in reducing premature mortality.
Figure 15:
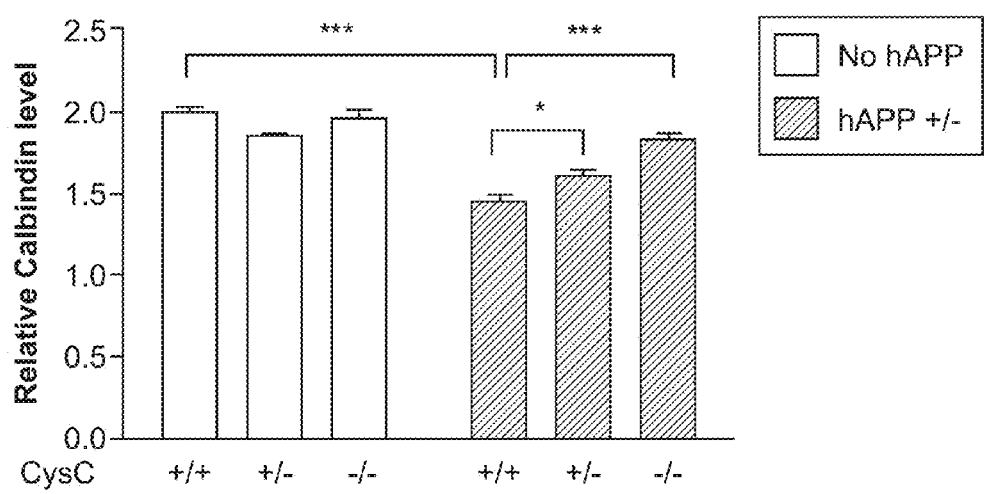
FIG. 15 depicts the effect of CysC reduction on calbindin depletion in the dentate gyrus (DG) of hAPP mice.
Figure 16:
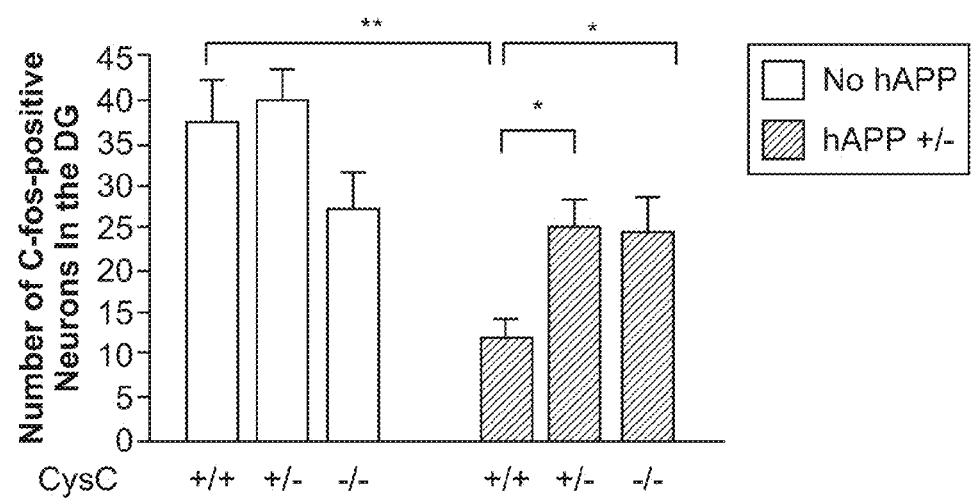
FIG. 16 depicts the effect of CysC reduction on C-fos depletion in the DG of hAPP mice.
Figure 17:
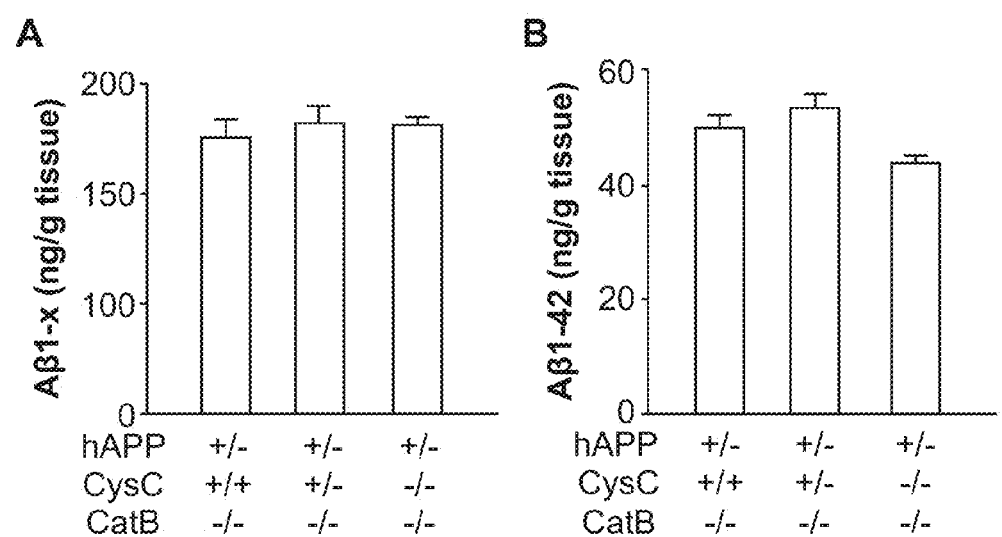
FIG. 17 depicts the effect of CysC reduction on Aβ levels in the absence of CatB.

FIGS. 12-17 depict additional results. FIG. 12 depicts results showing that Cystatin C reduction lowers soluble Aβ1-x and Aβ1-42 in young hAPP mice. FIG. 13 depicts results showing that Cystatin C ablation reduces the relative abundance of Aβ1-42 in young hAPP mice. FIG. 14 depicts results showing that Cystatin C reduction reduces premature mortality. FIG. 15 depicts results showing that CysC reduction ameliorates calbindin depletion in the dentate gyrus of hAPP mice. FIG. 16 depicts results showing that CysC reduction ameliorates C-fos depletion in the dentate gyrus (DG) of hAPP mice. FIG. 17 depicts results showing that the effects of CysC reduction on Aβ levels depend on the presence of CatB.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

The invention claimed is:

1. A method of reducing the level of human amyloid beta protein in a cell or a tissue, the method comprising contacting the cell or tissue with an antibody that selectively reduces cystatin C levels and/or activity in the cell or tissue, wherein reduction of cystatin C levels and/or activity results in a reduced level of human amyloid beta protein in the cell or tissue.

2. The method of claim 1, wherein the antibody specifically binds cystatin C.

3. The method of claim 2, wherein the antibody binds cystatin C with a dissociation constant (Kd) of less than $10^{-6}$ M.

4. The method of claim 2, wherein the antibody binds cystatin C with a dissociation constant (Kd) of less than $10^{-9}$ M.

5. The method of claim 1, wherein the antibody is a humanized antibody.

6. The method of claim 1, wherein the human amyloid beta protein is human amyloid beta$_{1-42}$.

7. The method of claim 1, wherein said cell is a neuron.

8. The method of claim 7, wherein said reduction of human amyloid beta protein levels reduces neuronal cell damage.

9. The method of claim 1, wherein the antibody selectively reduces cystatin C levels in the cell or tissue.

10. The method of claim 1, wherein the antibody selectively reduces cystatin C activity in the cell or tissue.

11. The method of claim 10, wherein the antibody neutralizes inhibition of cathepsin B cysteine protease activity by cystatin C.

12. The method of claim 1, wherein the antibody competitively inhibits binding of cystatin C to a cathepsin B polypeptide in the cell or tissue.

13. The method of claim 12, wherein the antibody competitively inhibits binding of cystatin C to a cathepsin B polypeptide in the cell or tissue by at least 50%.

14. The method of claim 12, wherein the antibody competitively inhibits binding of cystatin C to a cathepsin B polypeptide in the cell or tissue by at least 75%.

15. The method of claim 12, wherein the antibody competitively inhibits binding of cystatin C to a cathepsin B polypeptide in the cell or tissue by at least 90%.

16. The method of claim 1, wherein the antibody is a human antibody.

17. The method of claim 1, wherein the antibody is a chimeric antibody.

18. The method of claim 1, wherein the antibody is a monoclonal antibody.

19. The method of claim 1, wherein the antibody is a polyclonal antibody.

20. The method of claim 1, wherein the cystatin C is human cystatin C.

21. The method of claim 1, wherein, prior to the contacting, the cell or tissue has an increased level of human amyloid beta protein relative to a control cell or tissue.

* * * * *